(12) United States Patent
Eidelman

(10) Patent No.: US 9,914,103 B1
(45) Date of Patent: Mar. 13, 2018

(54) METHOD AND APPARATUS FOR SHOCKWAVES PROCESSING WITH LOW ACOUSTIC AND THERMAL ENVIRONMENTAL IMPACTS

(71) Applicant: Shmuel Eidelman, Rockville, MD (US)

(72) Inventor: Shmuel Eidelman, Rockville, MD (US)

(73) Assignee: Shmuel Eidelman, Rockville, MD (US)

( * ) Notice: Subject to any disclaimer, the term of this patent is extended or adjusted under 35 U.S.C. 154(b) by 0 days.

(21) Appl. No.: 15/264,787

(22) Filed: Sep. 14, 2016

(51) Int. Cl.
*B01J 19/10* (2006.01)
*B01J 3/08* (2006.01)
*G01N 31/12* (2006.01)
*G01N 25/44* (2006.01)
*C12N 1/06* (2006.01)

(52) U.S. Cl.
CPC ............. *B01J 3/08* (2013.01); *B01J 19/10* (2013.01); *C12N 1/066* (2013.01); *B01J 2219/089* (2013.01); *B01J 2219/0869* (2013.01); *B01J 2219/0877* (2013.01); *B01J 2219/19* (2013.01); *G01N 25/44* (2013.01); *G01N 31/12* (2013.01)

(58) Field of Classification Search
CPC ............. B01J 19/10; B01J 2219/0869; B01J 2219/0877; B01J 2219/089; B01J 2219/19; B01J 3/08; B01J 4/002; G01N 31/10; G01N 31/12; G01N 25/44; C12N 1/066
USPC .... 436/159, 160, 181; 422/94, 20, 186, 187; 204/157.15
See application file for complete search history.

(56) References Cited

U.S. PATENT DOCUMENTS

| | | | | |
|---|---|---|---|---|
| 4,207,154 A * | 6/1980 | Lemelson | ............... | B01J 3/08 204/157.41 |
| 5,588,357 A * | 12/1996 | Tomikawa | ............... | A23L 3/015 422/127 |
| 8,684,970 B1 * | 4/2014 | Koyfman | ............... | A61B 17/2251 604/140 |
| 8,840,835 B1 * | 9/2014 | Eidelman | ............... | A61L 2/02 204/157.15 |
| 9,475,027 B1 * | 10/2016 | Eidelman | ............... | B01J 4/002 |
| 2012/0205188 A1 * | 8/2012 | Fullerton | ............... | F02K 7/02 181/107 |

* cited by examiner

*Primary Examiner* — Maureen Wallenhorst

(57) ABSTRACT

A method for processing liquids and suspensions using shockwaves that includes providing an apparatus including a shockwaves generation and processing sections and a reaction products dumping tank or reservoir; placing media to be processed into the shockwaves processing section through continuous or intermittent injection; introducing a pressurizing gas into the shockwaves generation section; introducing a detonable mixture into the shockwaves generation section; causing formation of at least one of a shockwave within the shockwaves generation section by igniting the detonable mixture so that at least one of a shockwave propagates from detonation section into shockwaves processing section; utilizing physical, chemical, biological or mechanical effects of the shockwaves in the shockwaves processing section; purging detonation products and pressurizing gas from the shockwaves generation section into reaction products dumping tank; and repeating to achieving a pre-determined degree of processing liquids, liquid suspension, colloids, gels, pastes located in the shockwaves processing section.

21 Claims, 7 Drawing Sheets

METHOD AND APPARATUS FOR SHOCKWAVES PROCESSING WITH LOW ACOUSTIC AND THERMAL ENVIRONMENTAL IMPACTS

BACKGROUND

1. Field

The present invention generally directed to a method and an apparatus for processing using shockwaves or high amplitude acoustic waves.

2. Background

There is a critical need for efficient generation of high intensity shockwaves in liquids and suspensions for various processing applications. High pressure shockwaves propagating through a liquid can be utilized for killing microorganisms contained in the liquid, disrupting biological cells contained in the liquid suspension, enabling gene and drug transfer through cell walls, promoting chemical reactions in the liquids, increasing production of alcohol in bioreactor, and other applications. Depending on processing needs one may require different characteristics of shockwaves for specific processing goals. One of the methods of processing using shockwaves is described in U.S. Pat. No. 8,840,835 and U.S. Pat. No. 9,475,027. This method has the steps of injecting a reactive mixture into a shockwaves generation chamber, igniting a detonation wave that propagates through the reactive mixture and generating shockwaves in a chamber containing a liquid that is connected to the aft end of the shockwaves generation camber. When using this method, the process of detonation or rapid combustion of the reactive mixture leads to a significant increase of reacted gas pressure in the shockwaves generation chamber. Reacted gas is then purged rapidly through the purge valves or specially designed orifices reducing pressure in the shock generation chamber before injection of the new detonable mixture for the next shockwaves generation cycle. Unfortunately, rapid purge of high pressure reaction products produced during shockwave generation also creates shockwaves or strong acoustic waves in the exterior surroundings of the shockwaves generation apparatus resulting in very loud noise. In addition, rapid purge of high temperature reaction products through often small orifices used in the purge lines and in the purge valves, leads to high thermal loads and thermal erosion of these lines.

The invention is directed broadly to provide a method and apparatus for shockwaves processing with suppression of noise, reduction of thermal load and reduction of environmental pollution produced by the purge of high pressure and high temperature gas produced during shockwave generation process.

BRIEF SUMMARY

The invention is directed broadly to an improved method and apparatus for shockwaves processing with reduced noise, thermal load and pollution produced by intermittent purge of the high pressure and high temperature gas produced when detonation process or high reaction rate combustion are used to produce shockwaves that are used in processing. Reduction of noise, heat load and pollution produced during purge of high pressure high temperature gas is achieved by broadly including means that facilitate dumping or purging of the reaction products into a single or multiple tanks or reservoirs filled with sound and heat absorbing media such as liquid, gel, gas, mixture of gases, multi-phase media or any combination thereof. The following are examples without limitation of sound and heat absorbing media that can be used in shockwaves processing method and apparatus: water, saline water, antifreeze compounds, water mixed with antifreeze, Freon, air, air and water vapors, refrigeration cooling agent. To achieve absorption effect, the said tanks or reservoirs are either positioned separately from the shockwaves processing apparatus or fully or partially envelop the shockwaves processing apparatus or some of its elements and allow dumping of purged reaction products through conduits into the sound and heat absorbing media that fills the tanks or reservoirs.

Enabling absorption of sound, heat and pollution produced during shockwaves generation is critical and essential for allowing operation of the shockwaves processing apparatuses that are using rapid chemical reactions for shockwaves generations in an industrial environment. In an non limiting example of an operation cycle of the shockwaves generation cycle of the shock processing apparatus, the shock generation chamber if filled with a mixture of oxygen/methane at 2 MPa (mega pascals) pressure and 300° K temperature. Ignition and detonation of this mixture will produce gaseous reaction products with approximate pressure of 24 MPa and temperature of 4000° K. Because shockwave generation cycle period can be 1 to 2 seconds, 24 MPa and 4000° K reacted gases, which may contain some carbon particles, needs to be purged from the shockwave generation chamber in less than a second in order to allow injection of a fresh mixture of reactive gases for the next cycle of shockwaves generation. Rapid purge of reacted gases from 24 MPa pressure to 0.1 MPa atmospheric pressure before next injection of reactive mixture is for example enabled through a single or multiple purge lines and purge valves and it will result in laud noise in the external surrounding of the shockwaves processing system, heating and causing thermal erosion of the purge lines and purge valves. In addition, purged gases can contain small carbon particles and other environmentally harmful components. These undesirable effects will limit industrial use of the shockwaves processing systems that are using chemical reactions for shockwaves generation.

Dumping reaction products during shockwaves generation process into sound and heat absorbing media placed in a dumping tank is critical because it will significantly reduce adverse effects of the reacted gas purge. Invention can be implemented in alternative embodiments. In one embodiment a tank filled with water or other absorbing media is enveloping the shockwaves generation section of the shockwaves processing apparatus and the purge lines, purge valves and/or purge orifices are partially or fully immersed in absorbing media in the tank. In another embodiment entire shockwaves generation section of the apparatus is fully or partially immersed into a tank filled with absorbing media. In another embodiment purge lines and purge valve or orifice are immersed into liquid or multiphase media contained in a reaction products dumping tank placed separately from the shockwaves generation chamber. In another embodiment shockwaves processing apparatus is fully or partially immersed in an open reservoir filled with sound and heat absorbing media. In another embodiment each purge line, purge valve and/or purge orifice are equipped with a dumping tank filled with the same or different sound and heat absorbing media.

When for example without limitation water is used as sound and heat absorbing media the amount of water contained in the dumping tank is determined as a function of purge gas pressure, temperature and gas volume with the objective that the dumping tank water physical and chemical conditions after the purge will not change to a degree that will substantially affect its heat and sound absorbing capability. The water in the dumping tank can be refilled continuously or intermittently and the dumping tank can be filled fully or partially and exposed to atmospheric pressure or pressurized to pressure higher or lower than atmospheric pressure. Standard methods can be suitably selected by persons skilled in the art with the aid of no more than routine experimentation to determine shape and size and select materials for construction of the reaction products dumping tanks that will be used for absorption of sound, heat and pollution absorption produced during shockwaves processing apparatus operation. Larger volume dumping tanks will result in more effective sound and heat absorption.

During shockwaves generation cycle of shockwaves processing apparatus operation high pressure and temperature reaction products gas will be rapidly purged into for example water contained in a dumping tank creating gas bubbles and acoustic waves in water inside the tank. To further reduce the noise produced by the gas bubbles, their size and internal gas pressure can be controlled by allowing entry of the reacted gas into sound absorbing liquid through multiple orifices, through gas filters, metal or other materials grids or any other device that can break the reacted gas flow into multiple small gas streams resulting in generation of smaller and lower pressure bubbles. In addition to absorbing sound, water or other media in the dumping tanks will also absorb heat of the purged gas, reduce heat load on the purge lines and purge valves immersed in it and absorb some particles contained in the reaction products.

Exhausting of the high pressure reacted gas from the shockwave generation section into sound absorbing media will generate mechanical impulses. These mechanical impulses can be damped by known methods such as design of the mechanical structure, selecting structural material, adding shock absorbing dumpers and similar methods.

The sizes of reaction products dumping tanks and materials selected for their construction can be determined by standard methods and can be suitably selected by persons skilled in the art with the aid of no more than routine experimentation. To control temperature of the media in the dumping tanks the tanks can be equipped with active or passive cooling systems and absorbing media can be circulating between the reaction products dumping tank located near the shockwave generation system and a larger tank. When low cost media, such as water, is used for sound and heat absorption circulation of media may be not need and media can be just flushed through the dumping tank into a drain or water collection tank.

In one embodiment the shockwaves processing apparatus comprises a process control module, a shockwaves generation chamber, valves or other means for controlled injection of fuel, oxidizer and pressurizing gas, an igniter, an interface between the volumes of shockwaves generation and processing chambers, a shockwaves processing chamber with valves controlled inlet and outlet allowing continuous or intermittent injection of material to be subjected to shockwaves generated in the shockwaves generation chamber, a reaction products dumping tank filled with water that is injected and discharged from the dumping tank through inlet and outlet valves and a purge gas exhaust valve controlling discharge of gas from dumping tank. The dumping tank is positioned around the lower part of the shockwaves generation chamber and high pressure reacted gas generated in the shockwaves generation chamber is discharged into water that fills said tank through a small cross section tube and a purge valve.

The volume of the shockwaves generation chamber may range from $0.1$ $cm^3$ to $100$ $m^3$, but usually from $1$ $cm^3$ to $1$ $m^3$, the volume of the processing chamber may range from $0.1$ $cm^3$ to $100$ $m^3$, but usually from $1$ $cm^3$ to $1$ $m^3$ and the volume of reaction products dumping tank may range from $1$ $cm^3$ to $500$ $m^3$ but usually from $50$ $cm^3$ to $50$ $m^3$. Without limitation shockwaves generation chambers, processing chambers and reaction products dumping tanks can have cylindrical, conical, spherical, prismatic or other geometries for their external forms and internal volumes. In one embodiment both shockwave generation and processing chambers have cylindrical geometry with internal diameter from $0.01$ cm to $5$ m but usually from $0.1$ cm to $50$ cm and dumping tank have cylindrical geometry with internal diameter of $1$ cm to $50$ m but usually from $10$ cm to $10$ m. The length of cylinders for shock generation chamber, shock processing chamber and dumping tank can be from $1$ cm to $10$ m. Such a wide range of scales of implementation is critical for various scientific and industrial applications that include generation and utilization of shockwaves. Use of reacted gas dumping tank will enable generation of shockwaves in a shockwaves generation chamber at time intervals of $1$ millisecond to $30$ minutes, but usually at time intervals of $10$ milliseconds to $10$ minutes allowing reliable generation of shockwaves in processed liquids and exposing processed liquids to single or multiple shockwaves as needed for processing. Shockwaves generations at irregular intervals or single cycle shockwaves generation is also envisioned.

In another embodiment, the shockwaves processing apparatus comprises a process control module, shockwaves generation chamber, valves or other means for controlled injection of fuel, oxidizer and pressurizing gas, an igniter, a pressure relief valve, a shockwaves processing chamber with valves controlled inlet and outlet allowing continuous or intermittent injection of material to be subjected to shockwaves generated in the shockwaves generation chamber and a reacted gas purge conduit extending into reacted gas dumping tank filled with heat and sound absorbing media. In this embodiment the reaction products dumping tank is placed separately from the shockwaves generation section of the apparatus and a part of the reacted gas purge conduit is immersed into the absorbing media that fills reacted gas dumping tank. The reaction products purge valve is immersed fully or partially in absorbing media in the dumping tank. The dumping tank is equipped with gas venting valve that exhaust the reacted gas, that was purged into the absorbing media, into surrounding through a gas filter. The heat and sound absorbing media are introduced and ejected from the dumping tank through the inlet and outlet valves that ether controlled by the controller or set manually for need flow of liquid assuring stable temperature of the absorbing liquid during system operation. To assure controlled temperature regime for the liquid known heat control method can be used such as injecting colder liquid through the inlet valve of the dumping tank and/or cooling the external walls of the dumping tank. Standard methods can be suitably selected by persons skilled in the art with the aid of no more than routine experimentation to determine shape and size and select materials for construction of the reaction products dumping tanks and design the flow rate of absorbing liquid and design the dumping tank cooling methods.

In another embodiment, to provide heat and sound absorption for the shockwaves generation section including reactant supply lines, gas purge lines and ignition section, the shockwaves generation section in immersed into liquid (for example water) in reaction products dumping tank. Depending on shockwaves processing requirements the flow of gases and liquids into and out of the dumping tank and to and from purge lines and valves can be implemented with the use or without use of mechanically, eclectically or other types of controlled valves, gas and liquid filters and other methods that are used in industry for controlling, measuring, cleaning and other ways processing of gas and liquid flows. Also depending on system requirements dumping tank may not need for example water circulation and will be open to outside environment for releasing reacted gas that will be first purged into water.

In another embodiment the shockwaves processing system is placed underwater in a dumping tank with open or partially open top to allow purge of reaction products or pressurizing gases from the dumping tank into environment. In this embodiment any pool of water either natural or artificial can be used as a dumping tank for gases purged from the shockwaves processing system providing effective sound and heat absorption. Also running water such as streams or rivers can be used for immersion of the entire shockwaves processing system or some of its elements in order to facilitate absorption of sound and heat discharge as a result of shockwaves generation process. The shockwaves processing system can be also placed in the open top dumping tank when partially or fully immersed in the water or at any depth from the water surface as dictated by the system design and processing needs. Clearly system placement at depth will create back pressure on the purge valves or orifices which will affect system operation and can be taken into account in designing system operation parameters. In this embodiment the reactive gas dumping tank or pool can be formed by any body of water natural or artificial for example lake or river. One also can use ocean or sea water as sound and heat absorbing media.

The steps of the shockwaves generation, shockwaves transmission directly or through interface into processing chamber and detonation products discharge into reaction products dumping tank can be applied in the shockwaves processing apparatus once or multiple times depending on a variety of factors including safety requirements, the type of process to be performed and other factors.

BRIEF DESCRIPTION OF THE DRAWINGS

The present invention will now be described in more detail with reference to preferred embodiments of the invention, given only by way of example, and illustrated in the accompanying drawings in which.

DETAILED DESCRIPTION OF THE INVENTION

Figure 1:
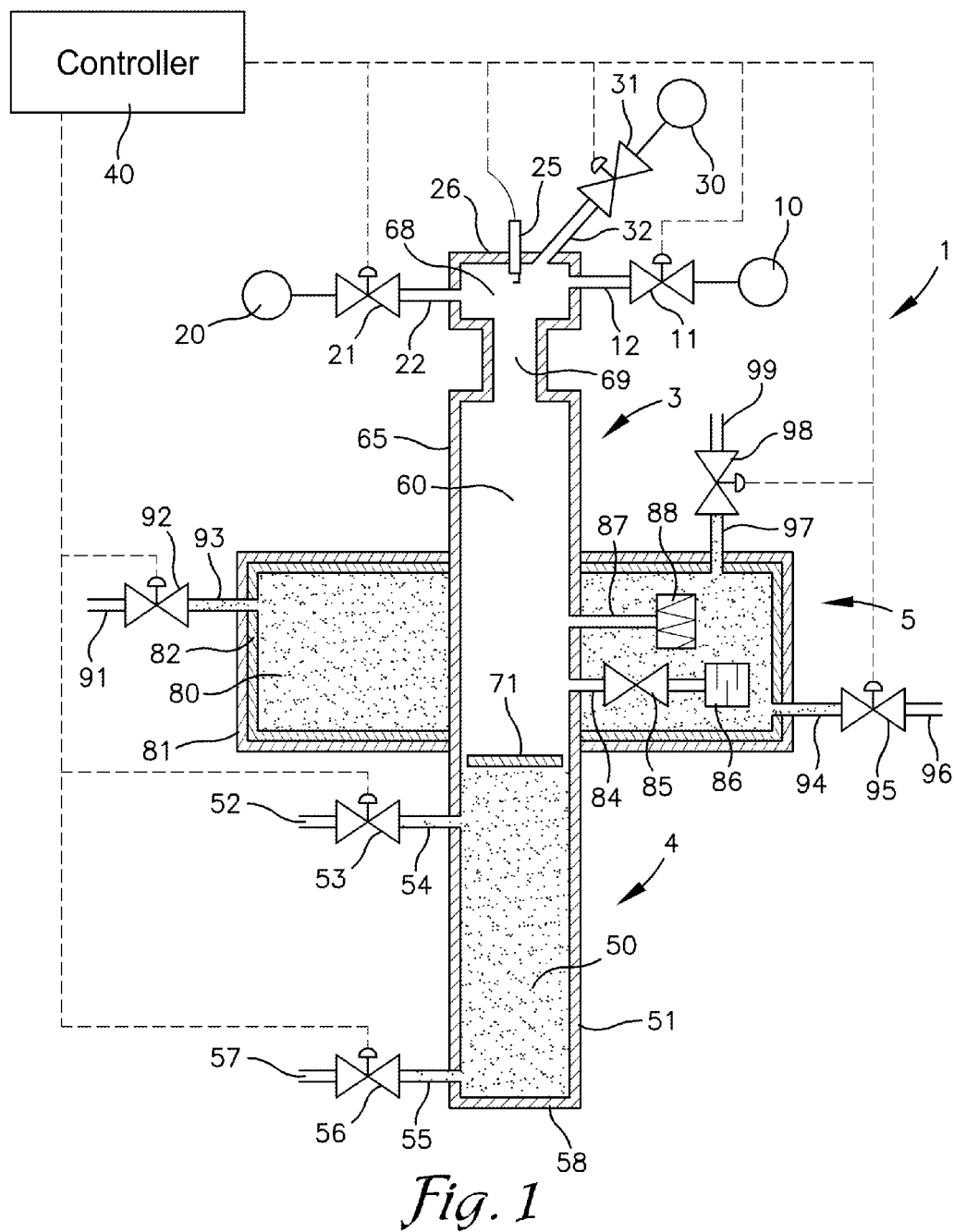
FIG. 1 is a schematic, cross-sectional illustration of a shockwaves processing apparatus with shockwaves generation and shockwaves processing sections where a section of the shockwaves generation chamber is immersed in a reaction products dumping tank.

The detailed description of exemplary embodiments herein makes reference to the accompanying drawings, which show exemplary embodiments by way of illustration. While these exemplary embodiments are described in sufficient detail to enable those skilled in the art to practice the inventions, it should be understood that other embodiments may be realized and that logical, chemical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In addition to their ordinary meaning, the terms set forth below and as used herein may be defined as follows:

"Shockwaves generation section" is the section of the shockwaves processing apparatus where shockwaves are generated including as a result of chemical reaction. It includes a shockwaves generation chamber, a reactives mixing chamber, an ignition chamber, valves, ignition and other system elements used for shockwaves generation and control of this section operation.

"Reaction products dumping tank", "dumping tank" or "dumping reservoir" is an enclosed or open vessel filled fully or partially with the sound and heat absorbing media that is used for absorbing sound and heat generated by the purge of reaction products or pressurizing gas from the shockwave generation section.

"Ignition chamber" is the section of the apparatus where the reactive mixture is ignited using a spark plug, laser, glow plug or any other mean that is able to initiate reaction of the reactive mixture located in this chamber.

"Reactives mixing chamber" or "mixing chamber" is the section of the apparatus designed to help mixing of oxidizer and fuel that are used for making reactive mixture. The function of mixing of reactive mixture components can be completed in a separate chamber or in a part of the shockwaves generation section;

"Shockwaves processing section" or "processing section" is the section of the apparatus to which the shockwaves generated in the shockwaves generation section are transmitted and which facilitate their propagation and utilization in physical, chemical, biological and mechanical processes. It includes a shockwaves processing chamber, valves and other systems used for control of this section operation.

"Shockwave", "shockwaves", "shock" or "pressure wave" when used in relation to processes in the shockwaves generation section of the apparatus all describe gas dynamic shockwaves or waves created by reaction of a detonable mixture that propagates with supersonic speed.

"Shockwave", "shockwaves", "pressure wave", "shock" or "wave" when used in relation to processes in the shockwaves processing section of the apparatus all describe hydrodynamic shockwaves or acoustic waves that propagate with sonic or supersonic speed in liquid, liquid suspension, colloid, gel, paste or solid media.

"Detonation" or "detonation process" are similar terms and are used herein to describe a physical and chemical phenomena characterized by a rapid chemical reaction that leads to the creation of a shockwave, shockwaves or pressure waves. When used in relation to the process within the shockwaves generation section, of the apparatus these terms are used to describe a reactive process that generates a shockwave, shockwaves or pressure waves. It is understood that, as a function of chemical composition, quantities, initial pressure and temperature, different types of physicochemical processes including deflagration, detonation, and transition from deflagration to detonation, rapid decomposition and combination thereof will lead to rapid pressurization of the shockwaves generation section and generation of shockwaves or pressure waves.

"Detonable mixture" as used herein, refers to single or multiple reactants that can undergo rapid chemical reactions including detonation, deflagration, rapid decomposition or combination thereof creating a shockwave or pressure wave. One example of a detonable mixture is the mixture of oxygen, hydrogen and nitrogen gases. Another example of a detonable mixture is a monopropellant such as nitrobenzene or nitroglycerin. Another example of a detonable mixture is high concentration hydrogen peroxide that can undergo explosive decomposition after injection into the shockwaves generation section of the apparatus. Selection of a suitable fuel and oxidizer or a single reactant to form the detonable mixture will be apparent to persons skilled in the art. Non-limiting examples of fuel reactants that can be used to form a detonable mixture include kerosene, gasoline, methane, natural gas, hydrogen, acetylene, and propylene. Non-limiting examples of oxidizer reactants that can be used to form the detonable mixture include oxygen, air, a mixture of oxygen and air, a mixture of oxygen and one or more inert gases such as nitrogen, argon or helium, hydrogen peroxide.

"Pressurizing gas" as used herein, refers to gas that is used to pressurize the shockwaves generation chamber after detonation or other reaction of detonable mixture that is generating shockwaves. One example of pressurizing gas is air. Another examples of pressurizing gas are nitrogen, oxygen, carbon dioxide, argon, mixture of air, nitrogen and water. Any other gas, mixture of gases or gas and liquid mixture that prevent self-ignition of detonable or reactive mixture injected into the shockwaves generation section can be used as pressurizing gas "Reaction products" as used herein, refers to chemical and physical products of reactions that are used to generate shockwaves in the shockwaves generation section. Reaction products also may contain pressurizing gas. Reaction products are purged from the shockwaves generation section after shockwaves are created. Non limiting example of reaction products is a mixture of carbon dioxide, carbon monoxide, water vapor, nitrogen, oxygen, "Shockwaves transmitting media", as used herein, refers to liquid, solid elastomers, colloids, gels, solid composite materials and other forms of material that can transmit hydrodynamic shock or acoustic waves. The examples of a shockwaves transmitting media are elastomer such as Aqualene, low density polyethylene, silicone rubber or solid plastic such as polystyrene, metals such as aluminum that have low acoustic attenuation coefficients.

"Processed liquid", "Unprocessed liquid" or "Media to be processed" as used herein, refers to liquids, colloids, suspensions, gels or pastes that may or may not include solid particles and/or gas bubbles or other components that can flow through the processing chamber in order to be processed by exposure to shockwaves or high amplitude acoustic waves that are generated in the shockwaves generation chamber.

"Impedance" means "acoustic impedance" that can be calculated by multiplying density and sound speed of the media.

"Membrane" is a part of the shockwaves generation section of the apparatus that transmits shockwaves or acoustic waves from the shockwaves generation section into the shockwaves processing section of the apparatus.

"Interface" is a part of the shockwaves processing section of the apparatus that is placed between the mostly gas in the shockwaves generation chamber and mostly liquid in the processing chamber and transmits shockwaves or acoustic waves from the shockwaves generation chamber to the shockwaves processing chamber. In difference with a "membrane" the "interface" is not attached to the walls of either detonation or processing chambers and can float or move with the liquid in the processing chamber.

FIG. 1 schematically illustrates an exemplary embodiment a shockwaves processing apparatus 1. The shockwaves processing apparatus 1, is configured for the repetitive generation of shockwaves to be transmitted into a shockwaves processing section for the shockwaves processing of media located in this section.

The shockwaves processing apparatus 1 includes a shockwaves generation section 3 in which shockwaves are generated, a shockwaves processing section 4 in which shockwaves are processing the media situated in this section and a reaction products dumping tank system 5 into which the reaction products produced during shockwaves generation and pressurizing gas are discarded. The shockwaves generation section 3 generally comprises a pressure vessel having a vessel wall 65 surrounding a shockwaves generation chamber 60. A pressurizing gas is injected into the ignition and mixing chamber 68 and shockwaves generation chamber 60 through a pressurizing gas feed line 32 extending from a pressurizing gas storage tank 30 through control valve 31. An oxidizer is injected into the ignition chamber 68 and shockwaves generation chamber 60 through an oxidizer feed line 12 extending from an oxidizer storage tank 10. An oxidizer control valve 11 on feed line 12 controls the flow of oxidizer into the ignition chamber 68 and shockwaves generation chamber 60. Fuel is injected into the ignition and shockwaves generation chamber through fuel feed line 22 extending from fuel storage tank 20 through fuel control valve 21. In the embodiment shown, the pressurizing gas feed line 32, the oxidizer feed line 12, and fuel feed line 22 extend through the wall of ignition and mixing chamber 68.

A spark plug 25 is mounted in the wall 26 and extends into the ignition chamber 68. The mixing and ignition chamber 68 and the shockwaves generation chamber 60 are connected through a conduit 69. Pressure relief conduits 87 and 84 are extending through the wall 65 of shockwaves generation chamber 60 into reaction products dumping tank 80. Pressure relief conduit 87 is capped with an air filter 88 and conduit 84 is attached to a one-way purge valve 85 connected to a silencer/filter 86.

A reaction products dumping tank system 5 generally comprises a dumping tank having a tank wall 81 surrounding a dumping tank chamber 80. Shown in FIG. 1. reaction products dumping tank wall 81 is enveloping a lower section of the shockwaves generation chamber wall 65 where the enveloped section is fully or partially immersed in the media contained in the reaction products dumping tank 80.

A sound and heat absorbing media is injected from a feed line 91 continuously or intermittently through a control valve 92 and through conduit 93 into dumping tank chamber 80. The sound and heat absorbing media is vacated from the dumping tank volume through conduit 94 extending through the wall 81 of the dumping tank, control valve 95 and drain line 96. The gas purged into the reaction products dumping tank is ejected from the dumping tank through conduit 97 extending through the wall 81 of the dumping tank 80, through controlled valve 98 and conduit 99. For better absorption of acoustic waves, the inner surfaces of the wall 81 may be covered with sound absorbing materials 82, such as silicone rubber, foamed polyethylene or similar. The sound and heat absorbing media is injected and discarded from the reaction products dumping tank 80 at the rates that are designed to maintain partial or full immersion of gas purge lines exits. Continuous flow of sound absorbing media through the dumping tank 80 allows maintenance of temperature of the media in the tank. As a function of purged gas amount media flow through the tank can be increased or decreased. In some instances, it will be sufficient to fill the reaction products tank just once to allow effective sound and heat absorption by the media in the tank. Flow rate through the tank is designed to maintain sound and heat absorbing properties of the dumping tank and can be calculated by persons skilled in the art using standard methods with the aid of no more than routine experimentation. As non-limiting example, water can be used as effective sound and heat absorbing media. Also ethylene glycol, propylene glycol, glycerol or mixture of these chemicals with water can be used as sound and heat absorbing media. Media that is able to attenuate sound emitting form the shockwaves generation chamber during the purge of high pressure reacted gas from the chamber and absorbed heat released by the high temperature purged gas can be used as sound and heat absorbing media.

The shockwaves processing section 4 generally comprises a vessel wall 51 surrounding a processing chamber 50. The processing chamber is separated from shockwaves generation chamber by an interface 71 that is placed between the processed media located in chamber 50 and reactive or reaction products or pressurizing gas filling the shockwaves generation chamber 60. Shown in FIG. 1 movable low attenuation interface 71 can be floating on the surface of the liquid in the chamber 50 or suspended in the liquid using known mechanical means. Methods for design and materials that can be used for movable interfaces are described in U.S. Pat. No. 9,475,027.

A raw unprocessed liquid or liquid suspension is injected from the inlet 52 through an inflow control valve 53 and inflow line 54 into the processing chamber 50. The processed liquid or suspension is exiting the processing chamber through the outflow line 55 connected to the control valve 56 and leaving the shockwaves processing section 4 via the outlet line 57. In FIG. 1 the unprocessed liquid inflow line 54 is located near the top and the processed liquid outflow line 55 at the bottom of the processing chamber 50.

A controller 40 is connected through electrical wires or wirelessly to control valves 11, 21, 31, 53, 56, 92, 95, 98 and spark plug 25 and is programmed to control the operation of these components and provide electrical power for their operation. In addition, controller can be connected to pressure, liquid level, and temperature sensors monitoring physical conditions of the processed media and media in the reaction product dumping tank at different locations of the shockwaves processing apparatus. These sensors are not shown in the FIG. 1.

An example of the shockwaves processing apparatus 1 shown schematically in FIG. 1 may have a cylindrically shaped ignition and mixing chamber 68 connected via a smaller cross section cylindrical tube to a cylindrical shockwaves generation chamber 60 with the similar diameter as ignition chamber. The shockwaves generation chamber 60 is connected to a cylindrically shaped processing chamber 50 with the same internal diameter as the shockwaves generation chamber. The reaction products dumping tank has a right hollow cylindrical shape, where its hollow center is filled with a lower part of the shockwaves generation chamber 60, thus part of the outside wall 65 and reaction products purge lines, purge orifices, valves and filter are immersed in the media contained in the tank 80. As an example of the dimensions of the system elements, the inner diameter of the ignition chamber 68 may be 2 cm with 1.5 cm height, the tube 69 connecting the ignition and shockwaves generation chambers may 5 cm long with 1 cm diameter. As an example the diameter of both shockwaves generation and processing chambers may be 2 cm, where the length of the shockwaves generation chamber is 51 cm and the length of the shockwaves processing chamber is 32 cm. As an example the inner diameter of the reaction products dumping tank is 36 cm and its height is 25 cm. Thus the volume of the ignition chamber 68 is approximately 5 cm$^3$, the volume of the tube 69 is approximately 4 cm$^3$, the volume of the shockwaves generation chamber 60 is approximately 150 cm$^3$, the volume of the shockwaves processing chamber 50 is approximately 100 cm$^3$ and the volume of the reaction products dumping tank is approximately 25.3 liters.

The walls 26 and 65 of the ignition 68 and the shockwaves generation 60 chambers may be made from temperature resistant high impedance material for example 1 cm thick high strength steel. The wall 81 of the reaction products dumping tank may be made from 0.2 cm thick low cost steel. For better absorption of acoustic waves the inner surfaces of the wall 81 may be covered with sound absorbing materials 82, such as 1 cm thick layer of silicone rubber, foamed polyethylene or similar. In FIG. 1 acoustic wave absorbing liner 82 is shown. The reaction product dumping tank wall 81 may be attached to the external wall 65 of the shockwaves generation chamber 60 proving a seal that contains the media that fills the dumping tank 80. The wall 81 of the reaction products dump tank is constructed from material that will contain sound and heat absorbing media and also providing mechanical strength to the structure to contain mechanical impulses and acoustic waves generated as a result of the purge of reacted or pressurizing gases into the absorbing media. Standard methods can be suitably selected by persons skilled in the art with the aid of no more than routine experimentation to attach walls 65 and 81 and to select material used for the reaction products dumping tank construction.

To lower losses of shockwave energy, the wall 65 forming the shockwaves generation chamber 60 may be made of a high acoustic impedance material such as tungsten-carbide-cobalt cermet with 5 mm thick wall. Other examples of high strength material with high temperature resistance and high acoustics impedance that can be used in construction of the shockwaves generation section 3 such as tungsten, Inconel, steel and tantalum. The wall 51 of the shockwaves processing section 4 may be made from high strength and high acoustic impedance materials for example 1 cm thick high strength steel. Other examples of high strength, high acoustic impedance materials that may be used for construction of the shockwaves processing section 4 include Inconel, steel, aluminum oxide, tungsten-carbide-cobalt cermet and other similar metals, cermets, and ceramic materials.

Standard methods can be suitably selected by persons skilled in the art with the aid of no more than routine experimentation to select materials that will contain high pressure, high temperature reaction products that will intermittently interact with the wall 65 of the shockwaves generation chamber 60 and high pressure shockwaves that will impact the wall 51 of the processing chamber 50. Also a combination of materials can be used to lower the cost, lower total weight or improve processing performance. For example, high strength carbon fiber composite material with a steel or other metals liner can be used for construction of the shockwaves generation and shockwaves processing chambers.

To prevent overheating of the shockwaves processing apparatus 1 as a result of heat generated by chemical reactions in the shockwaves generation process standard methods can be suitably selected by persons skilled in the art with the aid of no more than routine experimentation for cooling shockwaves generation chamber 60, valves, gas and liquid lines and other sections for the shockwaves processing apparatus 1. These methods can include passive cooling by increasing external surface area of walls 65 and 51, cooling using water or other cooling agent circulation, and cooling using flow of air or other gases. Standard methods can be suitably selected by persons skilled in the art with the aid of no more than routine experimentation to control temperatures of shockwaves generation and shockwaves processing sections. Control of temperature may include heating or cooling the shockwaves generation and shockwaves processing sections and their elements to achieve optimal performance characteristics.

Operation of the shockwaves processing apparatus 1 schematically shown in FIG. 1 starts with filling reaction products dumping tank 80 with the sound and heat absorbing media such as water. The tank 80 can be filed from inlet line 91 by opening inlet valve 92 through inflow line 93. The tank 80 can be completely or partially filled with the sound and heat absorbing media with the excess of media discarded through outlet line 94, valve 95 and line 96. The media that flows out of the tank from line 96 and be either discarded, collected for farther cleanup or processing or recirculated through the system. When filling the tank 80 with the absorbing media a small gas gap or multiple gaps may be left between the surface of the media and the top inner surface of the tank. This gas gap or gaps will allow accumulation of the purge gases that will rise to the top of the surface of the absorbing media in tank 80. Other methods can be also used for collecting purged gases such as incorporating a gas collection cavity into reaction products dumping tank design. During apparatus operation any gas released into the tank will raise to the surface of media in tank 80 and will be released through the exhaust line 97, control valve 98 and line 99. The control valve 98 may be constantly open, set to open at some purge pressure level or open intermittently by an electronic signal sent from controller 40. Purged gas exiting the system from line 99 can be released into the environment or captured for further processing.

At the next step raw unprocessed liquid or suspension is injected from the inlet 52 through valve 53 and inflow line 54 into the processing chamber 50. The outflow valve 56 remains closed allowing to fill the processing chamber 50 with unprocessed liquid. As a function of processing parameters injected unprocessed liquids can be cooled or heated to achieve optimal processing conditions or to enhance effectiveness of the shockwaves processing. When the shockwaves processing chamber is filled to designed level which may be indicated by an ordinary level sensor or assessed by the fill time for the know inflow rate, the valve 53 is closed and the pressurizing gas valve 31 is opened leading to pressurization of the shockwaves generation and processing chambers to designed processing pressure. The magnitude of the processing pressure is determined by the pressure and injection rate of the pressurizing gas that is injected from the pressurizing gas tank 30 through the valve 31 and the gas line 32. The processing pressure is also a function of opening time of valve 31, which is controlled by the controller 40, and the volume of the shockwaves generation chamber 60. For the embodiment shown in FIG. 1 part of the volume of the pressurizing gas will leak into reaction product dumping tank 80 through the orifice 87 and filter 88. Also if the pressure level in chamber 60 is higher than valve 85 set opening pressure value, valve 85 will open and the excess of pressurizing gas will be purged into products dumping tank 80 through the line 84, valve 85 and filter 86. The main function of filters 88 and 86 is to break the gas stream emitting from the orifice 87 and valve 85 into smaller streams that will create small bubbles in the media in tank 80. This function can be also achieved by placing a perforated screen at the exits of orifice 87 and valve 85.

Injection of the pressurizing gas through the valve 31 is critical and essential because it facilitates effective displacement of reacted gases from the shockwaves generation chamber, prevents self-ignition of the detonable mixture by separating hot reacted products from previous cycle from the newly injected detonable mixture, facilitates cooling of internal volume of the shockwaves generation chamber, helps removing water or other liquids from the area of the igniter which can disrupt ignition and reduces or prevent splash back from the processing chamber 50 into shockwaves generation chamber 60. Pressurizing gas may be for example compressed air. As a function of process requirements the pressurizing gas can be heated or cooled before injection into the shockwaves generation section. Pressurization and rapid cooling of the shockwaves generation section can be also achieved by injection of a liquid or liquids into high temperature environment of the shockwaves generation chamber. For example, and without limitation 2,3-dihydrodecfluoropentane that will rapidly evaporate when injected into high temperature environment of the shockwaves generation chamber can be used for this chamber pressurization. Pressurization and cooling of the shockwaves generation chamber will be also achieved by injecting multi-phase mixture of liquid/gas or liquid/solid/gas media which will convert fully or partially to gas when injected into shockwaves generation chamber. Injection of the pressurizing gas also allows effective control of designed average pressure in the system, which reduces the load on system elements as a result of reduction of pressure fluctuation. Pressurization may be also implemented using other gases such as oxygen, nitrogen or argon that when injected into detonation can quench chemical reaction and cool internal volume of the shockwaves generation chamber. The pressure level in chamber 60 after pressurization phase of the shockwaves processing cycle can be higher or lower than the initial pressure of reactive mixture injected in chamber 60 before initiation of shockwaves generating reaction.

The pressure relief valve 85 is set to open when pressure in the shockwaves generation chamber exceeds a certain set level allowing to maintain constant level of pressure for gas and liquid located in the internal volume of the shockwaves generation chamber 60 and the processing chamber 50. When chosen pressure is reached in the shockwaves generation chamber 60 the pressurizing gas valve 31 may be closed and fuel and oxidizer are injected into the shockwaves generation chamber 60 displacing the pressurizing gas that will flow through valve 85 and orifice 87.

The fuel and oxidizer are selected so that the mixture is detonable or reactive and their injection through the control valves 11 and 21 into ignition chamber 68 is metered by the controller 40. Triggered by a signal from the controller 40 the detonable mixture is ignited by the spark plug 25 initiating deflagration in the ignition chamber 68. From the ignition chamber 68 the deflagration wave is transmitted into shockwaves generation chamber 60 through conduit 69. Standard methods can be suitably selected by persons skilled in the art with the aid of no more than routine experimentation for selection of detonable mixture, design of ignition and mixing chamber 68 and providing necessary ignition energy to igniter 25 to initiate a deflagration wave that will rapidly transit into detonation wave in the shockwaves generation chamber 60. The selection of initial pressure and chemical composition of the detonable mixture will lead to formation of a shockwave of designed intensity that when transmitted through the interface 71 into processing chamber 50 will generate shockwaves or high intensity acoustic waves in the processed liquid resulting in a selected processing effect. Such effect may include killing microorganisms for liquid pasteurization or sterilization, lysis of cells that are suspended in liquid for pharmaceutical processing, initiation of chemical reaction, promotion of nucleation for chemical processing, deagglomeration of particles in particle/liquid suspension, homogenization of suspension, material milling or processing for other known effect caused by high intensity shockwaves or acoustic waves in liquids or suspensions.

The ignition chamber 68 is also serving as a mixing chamber for fuel and oxidizer. Homogenous mixture of fuel and oxidizer is very important for efficient ignition, transition from combustion to detonation and detonation process. Standard methods can be used for improving fuel and oxidizer mixing in the ignition chamber 68 and further in the shockwaves generation chamber 60. As a function of processing parameters reactants of reactive mixture such as oxidizer, fuel or both can be cooled or heated before injection into shockwaves generation chamber.

The leading shockwave transmitted through the interface 71 will partially transmit into the liquid in chamber 50 and partially reflect from the liquid surface back into the shockwaves generation chamber 60. The reflected portion of the shockwave will then reflect back from the walls of the shockwaves generation chamber 60 and the endwall 26 and will impact the surface of the processed liquid generating additional shockwaves and acoustic waves in the liquid and creating additional processing effects. Efficiency of these multiple reflections is a function of materials that are used for construction of the shockwaves generation and processing chambers, where material with high impedance such as tungsten, tungsten carbide, tantalum, Inconel and similar will lead to more efficient reflections and generation of multiple secondary shockwaves and materials with lower impendence such as aluminum, carbon composite, nylon and similar will generate less efficient reflections and reduce the number of the secondary shockwaves.

As a result of the detonation of reactive mixture during shockwave generation process the average pressure in the shockwaves generation chamber 60 will increase. When the average pressure in the shockwaves generation chamber reaches a preset value the pressure relief valve 85 will open. For example, using stoichiometric methane-oxygen mixture as a reactive mixture with the initial pressure of the reactive mixture of 2 MPa the average pressure in chamber 60 after shock generating detonation reaction will be over 24 MPa. Purging the reaction products directly into atmosphere will generate undesirable high amplitude shockwave and acoustic waves. Depending on the device volume the noise level during gas purge can exceed 160 dB (decibel) which will make this equipment hazardous to operate without ear protection gear or will require building a sound insulation chamber around the system. Also discharging very hot gas directly into atmosphere through an orifice or a purge valve will lead to thermal erosion of purge lines and purge valves. When gas is purged into media contained in the damping tank 80 acoustic signal and heat generated by the expanding reaction products will be absorbed because absorption media typically will have density and heat capacity significantly higher and temperature significantly lower than purged reaction products. After getting in contact with the media in tank 80 significantly cooled purged reacted gases will be exhausted into environment through valve 98 and opening 99.

Due to gas release through the valve 85 pressure in the shockwaves generation chamber 60 will rapidly decrease. Injection of the pressurizing gas controlled by the valve 31 will assure that pressure in the shockwaves generation chamber will not fall below a set pressure value, will assist in purging detonation products from the chamber, will assist in cooling wall internal surfaces and also will assure that any liquid products from the processing chamber or liquid from reaction products dumping tank that may backsplash into the shockwaves generation chamber will be pushed back. Avoiding liquid back splash is very important for reliable system operation because this liquid can interfere with the spark plug ignition system as well as deposit material on the inner walls of the shockwaves generation chamber.

Purging reaction products does not interfere with the shockwaves generation process because of the dissimilar times scales of these processes. For example, the pressure relief valve 85 can be selected to have an opening time as short as 30 milliseconds when the time of generation, propagation and reflection of the shockwave will be approximately 2 milliseconds which will assure that operation of the purge valve does not interfere with the shockwave generation process. Pressure relief valve may be a mechanical, solenoid, piezoelectric or any other type of valve able to open and purge the reacted products or pressurizing gas. Pressure relief can also be facilitated by selecting the size of opening 87 or orifice so that during detonation very small amounts of gas will be exhausted thought this opening due to the short duration of the process and small size of the opening, thus most of the detonation products will be exhausted after shockwaves are transmitted into liquid in the processing chamber 50. Exhausted gases can be directly released into atmosphere via valve 98 and line 99 or can be captured, filtered and release into the surrounding atmosphere when not harmful.

After pressure in the shockwaves generation chamber 60 drops to a preset value, the pressure relief valve 85 closes, sealing the volume of the chamber 60. At this point, the steps of pressurization, injection of the detonable mixture and detonation will be repeated to generate another set of shockwaves. The shockwaves generation steps can be repeated at selected frequency to obtain the best processing effect for the chosen application. Thus each fill of the unprocessed material introduced into the shockwaves processing section 50 can be subjected to multiple cycles of shockwaves generation produced by the operation of the shockwaves generation section. In fact, the procedure of introducing the pressurizing gas, followed by introducing detonable mixture, causing formation of at least one shockwave and venting detonation products and pressurizing gas into dumping tank is repeated as many times as necessary for achieving a pre-determined degree of processing liquids, liquid suspension, colloids, gels, and pastes located in the shockwaves processing section.

Repeated purge of high temperature reaction products into the tank 80 can lead to heating of the media that is filling this tank. Temperature of the media in tank 80 can be controlled by controlling the flow rate of the sound and heat absorbing media through the tank 80 and its temperature at the inlet 93. Also standard methods can be used to cool or heat up the wall 81 of the tank externally in order to control the media temperature in tank 80.

The frequency of shockwaves generation section operation is controlled by the controller 40. Multiple pressure relief openings and valves can be used to facilitate rapid pressure relief and detonation products purge. Also single or multiple valves can be used for injection of reactive mixture and pressurizing gas into shockwaves generation section 3 and single or multiple valves can be used for filling the processing chamber 50. Filling shockwaves generation chamber with pressurizing gas allows repeatable generation of detonation waves at 0.001 Hz to 1000 Hz wave generation frequencies. As a function of processing needs the liquid or suspension located in the processing chamber 50 can be subjected to a single or multiple shockwave generation cycles. After processing is completed unprocessed liquid in injected into chamber 50 through valve 53 and processed liquid is ejected through valve 56. Timing of valves 53 and 56 opening and closure is controlled by the controller 40 and can be designed to facilitate designed exposure of the processed liquid to the shockwaves. Flow of the unprocessed liquid through the inlet 54 and the outlet 55 can be continuous, when shockwaves generation process is intermittent. In this case the flow rate of the unprocessed liquid will be adjusted to allow designed exposure to intermittent shockwaves generated in the shockwaves generation chamber.

Figure 2:
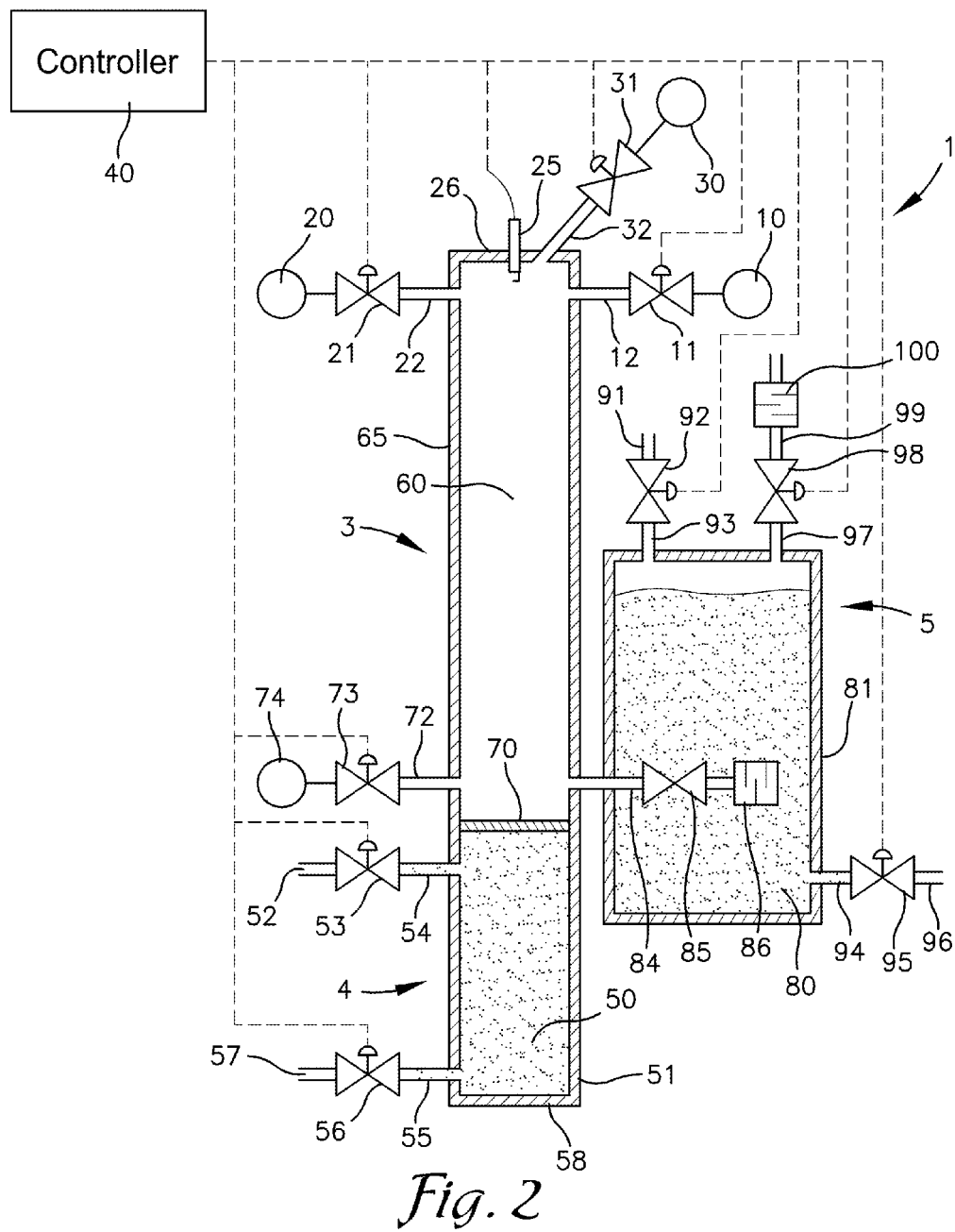
FIG. 2 is a schematic, cross-sectional illustration of a second embodiment of the shockwaves processing apparatus in which reaction products purge valve is immersed in reaction products dumping tank.

An alternative embodiment of a shockwaves processing apparatus 1 is shown in FIG. 2 having a reaction products purge section 5 located apart from the shockwaves generation section 3. In describing the embodiment of the shockwaves processing apparatus 1 shown in FIG. 2 and the additional embodiments shown in subsequent figures, common elements may be identified by the same reference numbers used in describing the embodiment shown in FIG. 1. In FIG. 2 the reaction products purge line 84 is extended from the shockwaves generation chamber 60 into reaction products dumping tank 80 that is located separately from the shockwaves generation section 3. The absorbing media is supplied into the tank 80 through line 91, valve 92 and inlet 93 located at the upper part of the wall 81 and expelled from the tank 80 from the outlet 94, valve 95 and line 96. The opening of the valves 92 and 95 is controlled by the controller 40 and ether intermittent or continuous. Controller 40 is also supplies power to all the valves and ignition. The flow into and out of the tank 80 is controlled so that a layer of gas is maintained at the top of the inner volume of the tank 80 allowing accumulation of the purged gas which is vented through line 97, valve 98, line 99 and gas filter 100 into environment. Other alternative means can be used to allow venting of purge gas into environment for example providing multiple opening at the top of tank 80.

In FIG. 2 the shockwaves generation section 60 and the shockwaves processing section chamber 50 are separated by a solid membrane 70 that is able to contain pressure in chamber 60. Thus pressure in chamber 50 is independent of pressure in chamber 60.

The membrane 70 is designed to seal fully the internal volume of chamber 50 when shockwaves generation chamber is pressurized. The membrane 70 can be made from materials that allow effective transmission of the shockwaves such as elastomer Aqualene, silicone rubber or solid plastic such as polystyrene that have low acoustic attenuation coefficients. Membrane 70 can also be made from metal or composite materials. Standard methods can be suitably selected by persons skilled in the art with the aid of no more than routine experimentation to protect elastomer from heat exposure from the detonation products. Metals have usually higher acoustic attenuation coefficient and higher strength and thermal stability than plastic or elastomers, thus using metals for construction of membrane 70 would minimize the thickness of the membrane. To contain high pressures generated in chamber 60 one can choose membrane made of high strength metals and metal alloys.

The membrane 70 is designed to contain the gases in the shockwaves generation chamber 60 and sustain the pressure difference between the chambers 60 and 50 that can develop during apparatus operation. In FIG. 2 shown feed the line 72 and the valve 73 that allow injection of water or other liquid with high heat capacity over the membrane 70 from liquid the source 74. Injection of suitable amount of liquid will create a layer of liquid covering fully or partially the membrane 70 surface which will not interfere significantly with the shockwave transmission through the membrane and protect the membrane 70 from exposure to high temperature reactive products in the chamber 60. Standard methods can be used to design the membrane 70 so that it will seal the gases in the shockwaves generation chamber 60 and sustain the pressure difference between the chambers 60 and 50, be impermeable to gas in the chamber 60 and cooling liquid injected through the valve 72. Other methods for protection of the membrane 70 from heat of reaction products can include coating the surface of the membrane 70 with a layer of heat resistive materials, timing the shockwaves generation cycle to allow cooling of the membrane between the cycles and other standard methods that can be suitably selected by persons skilled in the art with the aid of no more than routine experimentation.

In the embodiment illustrated schematically in FIG. 2 the wall 65 of the shockwaves generation chamber 60, wall 51 of the processing chamber 50 and the wall 81 of dumping tank 80 are cylindrical and one can use walls of different geometries for these chambers. For example, one can use a spherical geometry for wall 81, converging diverging cylindrical geometry for wall 65 and converging cylindrical geometry for wall 51. The walls 65 and 51 are preferably made from high strength, high thermal resistance and high impedance material such a high strength steel, Inconel, tungsten carbide and similar. The wall 81 just need to contain sound and heat absorbing media and can be made from plastic material such as polyethylene or polycarbonate. Wall 81 can be also made from steel.

An example of the shockwaves processing apparatus 1 shown schematically in FIG. 2 may have a cylindrically shaped shockwaves generation chamber 60 from the endwall 26 to the membrane 70 with a cylindrically shaped processing chamber 50 from the membrane 70 to the distal endwall 58. The inner diameter of the shockwaves generation chamber 60 may be 40 cm extending from the endwall 26 to the membrane 70 an internal height or length of 400 cm resulting in a volume of the shockwaves generation chamber 60 of approximately 0.5 $m^3$. The processing chamber 50 may be cylindrical that may have inner diameter 40 cm and extends from the membrane 70 to the distal end 58 of the processing chamber 50. An internal height or length of the shockwaves processing chamber 50 may be 200 cm resulting the internal volume of the processing chamber 50 of approximately 0.25 $m^3$.

To achieve focusing of the shockwaves the shockwaves generation chamber can have a converging geometry where the radius of the cylindrical wall 65 will converge from 40 cm in its middle cross section to 10 cm in the cross section connected to the membrane 70. In this case the processing chamber 50 will have cylindrical shape with diameter of 10 cm from the membrane 70 to the end wall 58. Focusing of shockwaves can be used to obtain shockwaves in the processing chamber with peak pressures substantially higher than Chapmen-Jouguet pressure that are characteristic for detonable mixtures. Focusing of shockwaves can be also used in the processing chamber 50, where the chamber wall 51 can have a frusta-conical shape converging for example from 10 cm diameter at the membrane to 5 cm at the distal end 58. Converging or diverging geometries can be used to ether amplify or reduce the peak pressure of the shockwaves or acoustic waves in the shockwaves generation and/or shockwaves processing chambers. Design of shockwaves generation and processing chambers can be accomplished using standard methods that can be suitably selected by persons skilled in the art with the aid of no more than routine experimentation.

Figure 3:
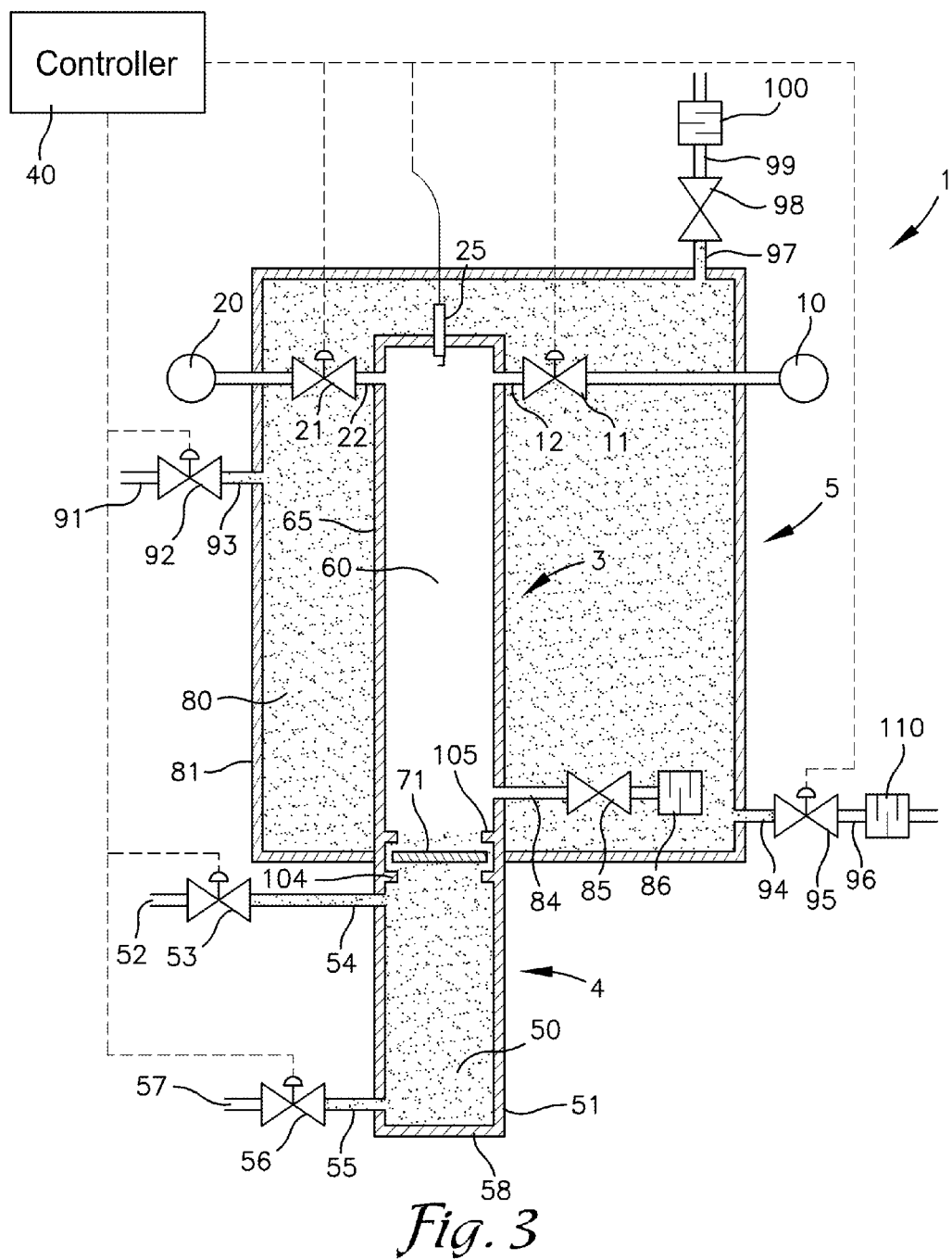
FIG. 3 is a cross-sectional schematic view of a third embodiment of the shockwaves processing apparatus in which entire shockwaves generation section is immersed into reaction products dumping tank.
Figure 3A:
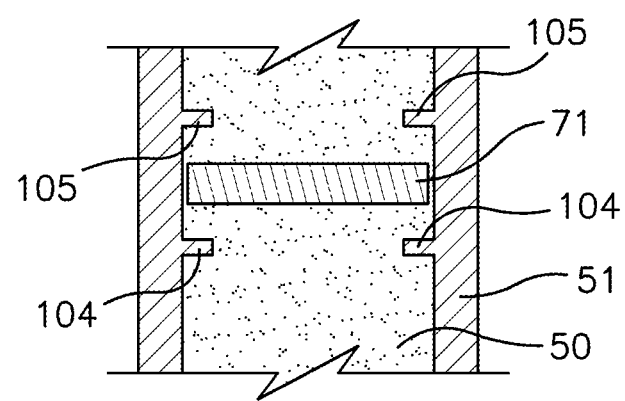
FIG. 3a is a schematic, cross-sectional illustration of a third embodiment of the shockwaves processing apparatus in the area of interface showing interface immersed in liquid and motion limiting rings.

An alternative embodiment of the shockwaves processing apparatus 1 is shown in FIGS. 3 and 3a. In FIG. 3 the shockwaves generation chamber 60 and the processing chamber 50 are cylindrical with the same inner diameter and a floating interface 71 is positioned between the chambers 60 and 50. In FIG. 3 the reaction products purge section 5 is enveloping the shockwaves generation section 3. The absorbing media is supplied into the tank 80 through the line 91, valve 92 and inlet 93 located at the upper part of the wall 81 and expelled from the tank 80 from the outlet 94, valve 95, line 96 and filter 110. Opening of the valves 92 and 95 is controlled by the controller 40 and is ether intermittent or continuous. The flow into and out of the tank 80 is controlled so that a layer of gas is maintained at the top of the inner volume of the tank 80 which will allow accumulation of the purged gas vented through the line 97, valve 98, line 99 and gas filter 100 into environment. As shown in FIG. 3 valves 21, 11 and 85 are immersed in media located in the tank 80. The alternative embodiment shown in FIG. 3 does not use pressurizing gas for shockwaves generation process In FIG. 3a shown a floating interface 71 which movements are limited by the rings 105 and 104 that have smaller diameter than the inner diameter of the chamber 50. During operation of the shockwaves processing apparatus 1 some liquid from the processing chamber can seep over the interface 71 as shown in FIG. 3a. Interface motion limiting ring 105 will be also beneficial in limiting flow of processed liquid into shockwaves generation chamber during unprocessed liquid injection. Ring 104 will limit flow of liquid located on the top of the interface 71 during detonation and detonation products purge phases of the shockwaves generation cycle. In addition to using the rings 105 and 104, limiting upwards and downwards motion of the interface 71 can be achieved with other mechanical means such as pins placed on the wall 51 or a local reduction of the inner diameter of the chamber 50. Placing some liquid over the surface of the interface 71 can be beneficial for protection of the interface from the heat load produced by the detonations. When the density of the interface 71 is lower than the density of the media located in the chamber 50 one can use a motion limiting ring 105 and when it is higher one can use ring 104.

It is preferable that the interface 71 is made from an elastomer that has low acoustic impendence and low acoustic attenuation parameters. Examples of elastomers that can be used to make the interface 71 include polyethylene, polyurethane, Nylon or ethyl vinyl acetate that have impedances comparable to the impedance of water. The interface 71 can be also made from materials that have high impedance and high mechanical strength such as metals, where shockwave transmission efficiency is achieved because in this case material strength will allow making the interface 71 thin.

Figure 4:
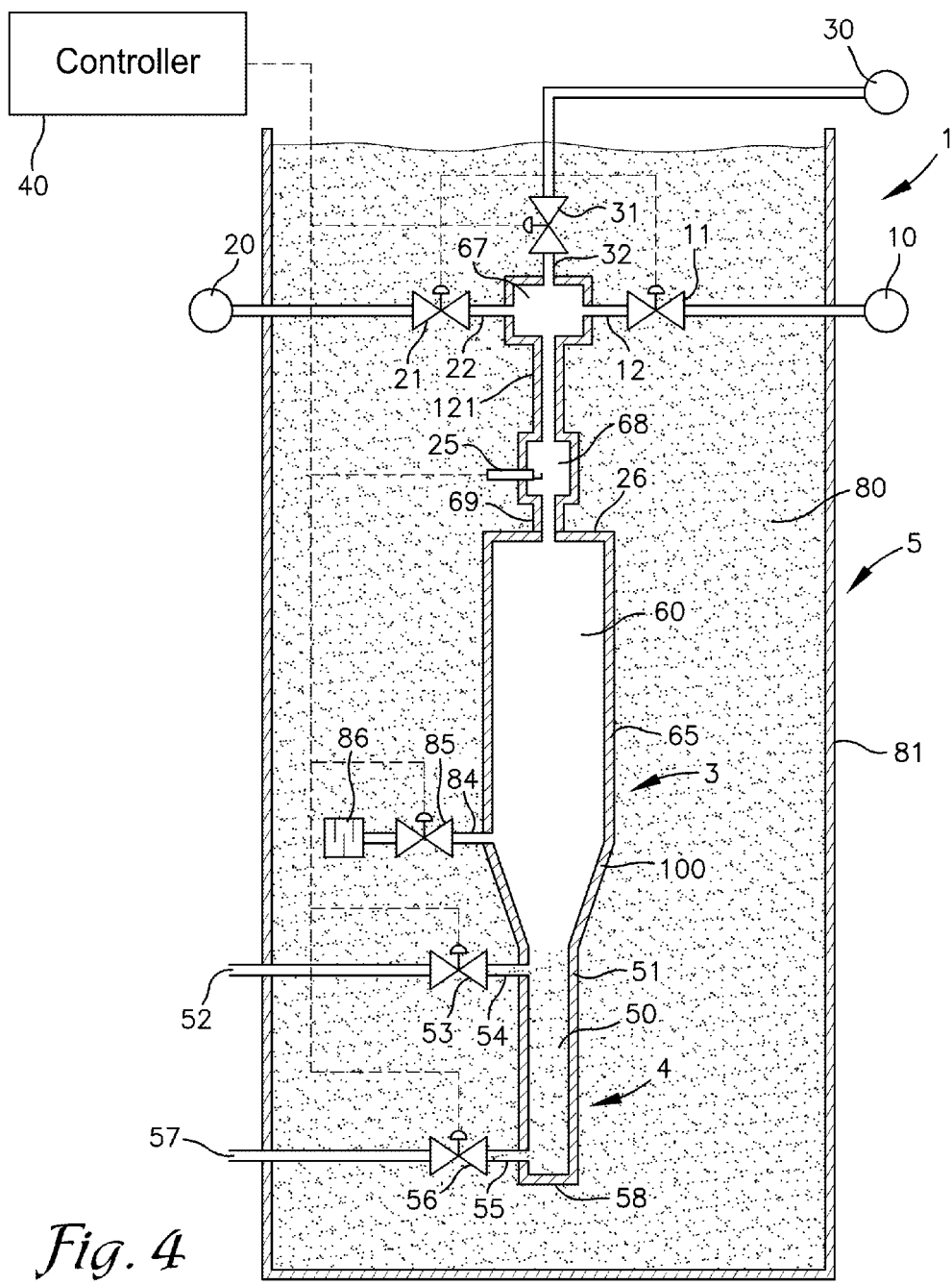
FIG. 4 is a cross-sectional schematic view of a fourth embodiment of the shockwaves processing apparatus where entire shockwaves processing system is immersed in reaction products dumping tank.

An alternative embodiment of the shockwaves processing apparatus is shown in FIG. 4. In FIG. 4 for heat and sound absorption the shockwaves processing system is placed underwater in the dumping tank 80 which has open or partially open top to allow purge of reacted gases from the dumping tank into environment. In this embodiment any pool of water either natural or artificial can be used as a dumping tank for the reacted gases purges from the shockwaves processing system providing effective sound and heat absorption. The shockwaves processing system can be placed in the open top dumping tank when partially or fully immersed in water or at any distance from the water surface as dictated by the system design and processing needs. Placement at substantial depth will create back pressure on the purge valves or orifices which will affect system operation may be taken into account when designing system operation regimes. In this embodiment the reactive gas dumping tank or pool can be formed by any body of water natural or artificial for example lake or river. One also can use ocean water as sound and heat absorbing media.

In FIG. 4 shockwave generation section 3 and shockwaves processing section 4 are immersed in the media in the reaction products dumping tank 80, where controller 40 and supply tanks 10, 20 and 30 can be positioned ether outside or inside the tank 80. The volume of water or other sound and heat absorbing media in the tank 80 may be chosen so that the absorbing media will retain its absorbing properties during operation of the shockwaves generation section 3.

In FIG. 4 pressurizing gas is injected through a pressurizing gas a feed line 32 extending from pressurizing gas storage tank 30 through control valve 31 into a mixing chamber 67 connected through a tube 121 to an ignition chamber 68 which is connected through a tube 69 with a shockwaves generation chamber 60 and a converging nozzle 100. An oxidizer is injected through an oxidizer feed line 12 extending from an oxidizer storage tank 10 into the mixing chamber 67 connected through the tube 121 to the ignition chamber 68 which is connected through the tube 69 with the shockwaves generation chamber 60. An oxidizer control valve 11 mounted on the feed line 12 controls the flow of the oxidizer into the shockwaves generation chamber 60. Fuel is injected through a fuel line 22 extending from a fuel storage tank 20 through a fuel control valve 21 into the mixing chamber 67 connected through tube 121 to the ignition chamber 68 which is connected through tube 69 with the shockwaves generation chamber 60. In the embodiment shown controlled, simultaneous or with a delay injection of oxidizer and fuel into the mixing chamber 67 will promote mixing of these reactive components creating a detonable mixture that will flow through tube 121 into ignition chamber 68 and further through tube 69 into the shockwaves generation chamber 60. Design of a mixing chamber that assures effective mixing of fuels and oxidizers can be suitably selected by persons skilled in the art with the aid of no more than routine experimentation.

In FIG. 4 the main volume of the shockwaves generation chamber 60 is connected to the shockwaves processing chamber 50 through a converging nozzle 100 and there is no interface or membrane between shockwaves generation and shockwaves processing chambers. Thus shockwaves generated in the chamber 60 will propagate through the nozzle 100 and impact media located in the chamber 50 generating shockwaves or acoustic waves that will propagate through the chamber 50. The nozzle 100 is conical and is converging from the diameter of the shockwaves generation chamber 60 to the diameter of the processing chamber 50. The convergence angle of the nozzle 100 can be designed to provide the most efficient amplification of the shockwaves peak pressure with minimal losses of shockwaves energy. Generally, and without limitations, convergence angles between 5 degrees to 60 degrees will provide efficient focusing of the shockwaves generated in chamber 60. Design of the nozzle 100 that assures effective focusing of the shockwaves propagating from the chamber 60 into chamber 50 can be suitably chosen by persons skilled in the art with the aid of no more than routine experimentation. Other elements, operation and materials used for construction of the embodiment shown in FIG. 4, are the same or similar to these described for the embodiment shown in FIG. 1.

A critical benefit of the embodiment shown in FIG. 4 is that use of large volume reaction products dumping tank with an open top simplify system operation because there is no need of monitoring and maintaining flow of sound and heat absorbing media. At the same time a large volume of sound absorbing media which is typically water allows effective absorption of sound and heat produced during shockwaves generation process.

The mixing chamber 67 assures that ignition chamber 68 will be filled with well mixed reactive mixture which when ignited by the spark plug 25 or other igniter will create a reaction wave that will rapidly transit into the detonation wave in the shockwaves generation chamber 60. Also injection of the pressurizing gas into the mixing and ignition chambers after the detonations assures cooling and cleaning these chambers which prevents self-ignition in the next cycle and improves spark discharge reliability.

Figure 5:
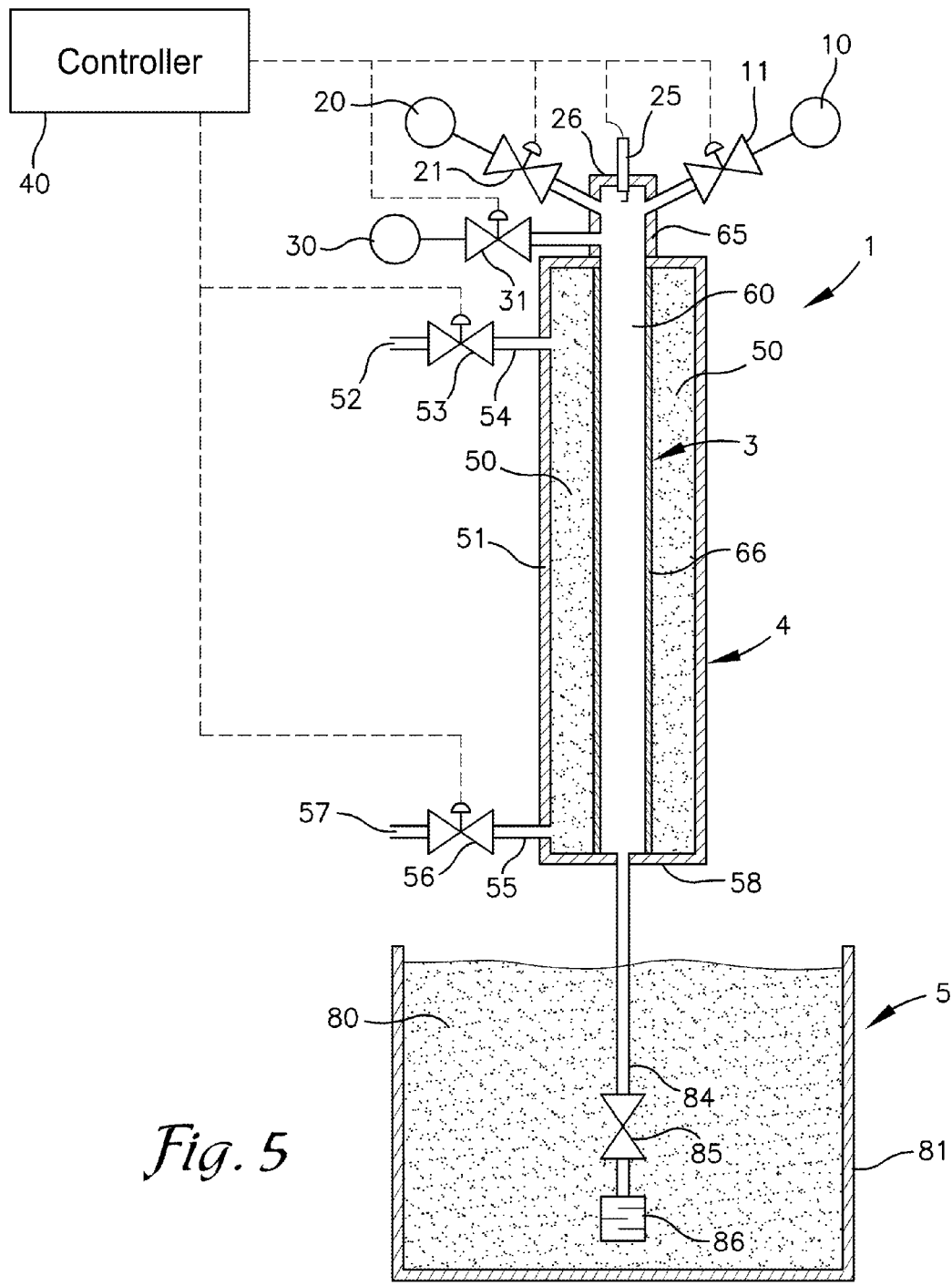
FIG. 5 is a cross-sectional schematic view of a fifth embodiment of the shockwaves processing apparatus where the shockwaves generation chamber is an inner cylindrical section of the shockwaves processing chamber and the purge line with the purge valve are immersed in reaction products dumping tank.

In the embodiment shown schematically in FIG. 5 the sound and heat absorption of the purged reaction products is accomplished by immersing the purge line 84, purge valve 85 and gas filter 86 into an open top reaction products dumping tank 80 with cylindrical tank wall 81. The cylindrical walls of a shockwaves generation section 3 are made from two cylindrical sections 65 and 66, where the wall section 65 is preferably made from high impedance materials such as steel, Inconel, tungsten carbide and the section 66 is preferably made from a low impedance material such as aluminum, carbon or silica based composites, ceramic and ceramic based composite materials and other materials designed to contain multiple detonations and where the wall section 66 is designed to allow efficient shockwaves transmission into a processing chamber 50. Another example of a material with high tensile strength and low impendence that allows efficient transmission of shockwaves that can be used for construction of the wall section 66 of the shockwaves generation section 3 is carbon composite material. In this case the inner walls of the shockwaves generation chamber 60 can be coated or cladded with metal, ceramic or other material with high thermal stability to protect carbon and elastomeric materials of the carbon composite from exposure to high temperature detonation products and from oxidation.

Shown in FIG. 5 the external surface of the wall 66 is fully or partially immersed into the processed media contained in the chamber 50. Shown in FIG. 5 the cylindrical wall 51 of the processing chamber 50 can be made from high acoustic impedance materials such as steel or tungsten carbide to enhance efficiency of reflections of the shockwaves emitted through the wall 66 of the shockwaves generation chamber which will cause additional exposure to the shockwaves to the material located in the chamber 50. Alternatively, the cylindrical wall 51 of the processing chamber 50 can be made from the materials such as aluminum, nylon, polyethylene, acrylic and other polymers, carbon based composite and other low acoustic impedance materials in order to reduce reflections of the shockwaves emitted through the wall 66. Designing the shockwaves processing apparatus 1 for the reduced reflections from wall 51 may be necessary for processing materials that are sensitive to the shockwaves or acoustic waves with a particular peak pressure and positive phase duration. Certain types of small microorganisms can be killed when exposed to the shockwaves with high pressure, for example 200 MPa, and short positive phase duration, for example 5 µsec, that can be emitted by shown in FIG. 5 the shockwaves generation section 3. When the wall 51 is made from a high impedance material such as steel incident waves transmitted by the wall 66 will be reflected back into the chamber 50 where they can interact with other emitted shockwaves which can create cavitation in the processed liquid or create a modified waves pattern. Then material of the wall 51 is selected to have impedance equal or similar to the materials located in the processing chamber 50 the reflections of the shockwaves will be weakened which will result in processing affected mostly by the incident waves emitted from the chamber 60. The reaction products dumping tank wall 81 can be made from plastics such as polyethylene, Plexiglas, polycarbonate or similar materials. Other elements, operation and materials used for construction of the embodiment shown in FIG. 5, are the same or similar to these described for the embodiment shown in FIG. 1.

A critical benefit of the embodiment shown in FIG. 5 is that its construction leads to the short shockwaves propagation distances, which allows for the more uniform exposure of the processed liquid to the shockwaves even if the shockwaves attenuation coefficient in the processed liquid is relatively large. In the embodiment shown in FIG. 5 when detonation wave is propagating along the inner wall 66 of the shockwaves generation chamber 60 it will create a shockwave or a strong acoustic wave in the processed liquid located along the outer surface of the wall 66. This shockwave or acoustic wave will have cylindrical geometry and its decay will comprise from the attenuation in liquid due to absorption and scattering and decay due to geometric spreading. Reducing the distance between the outer surface of the wall 66 and inner surface of the wall 51 one can minimize both geometric decay and acoustic or shockwaves absorption in the liquid. The embodiment shown in FIG. 5 can be especially beneficial for processing liquids or suspension with large attenuation coefficients as compared with water.

Another advantage of the embodiment shown in FIG. 5 is that it allows a simple scale up of the processing systems by increasing the length of the shockwaves processing apparatus 1. The alternative embodiment shown in FIG. 5 will allow generation and emission through the wall 66 shockwaves with peak pressure and impulse that will vary along the length of the wall 66. To allow uniform exposure of processed material to shockwaves one can control the flow of liquid through the volume of chamber 50 in order to assure uniform processing.

Another advantage of embodiment shown in FIG. 5 is that immersion of the shockwaves generation section wall 66 into the liquid in the chamber 50 will lead to cooling of this section of the wall by the flow of the processed liquid and at the same time to heating of the processed liquid by the heat emitted from the shockwaves generation chamber.

It is also envisioned that multiple shockwaves generation chambers can be inserted into a processing chamber where the external surfaces of the walls of these shockwaves generation chambers are fully or partially immersed into the processed media contained in the shockwaves processing chamber. In this implementation the shockwaves in the shockwaves generation chambers will be generated simultaneously, sequentially or in timed manner that in turn will generate shockwaves that will propagate through processed media and undergo constructive or destructive interference that will be used for improved effects in some applications such as particle deagglomeration, cleaning, and cell lysis.

Figure 6:
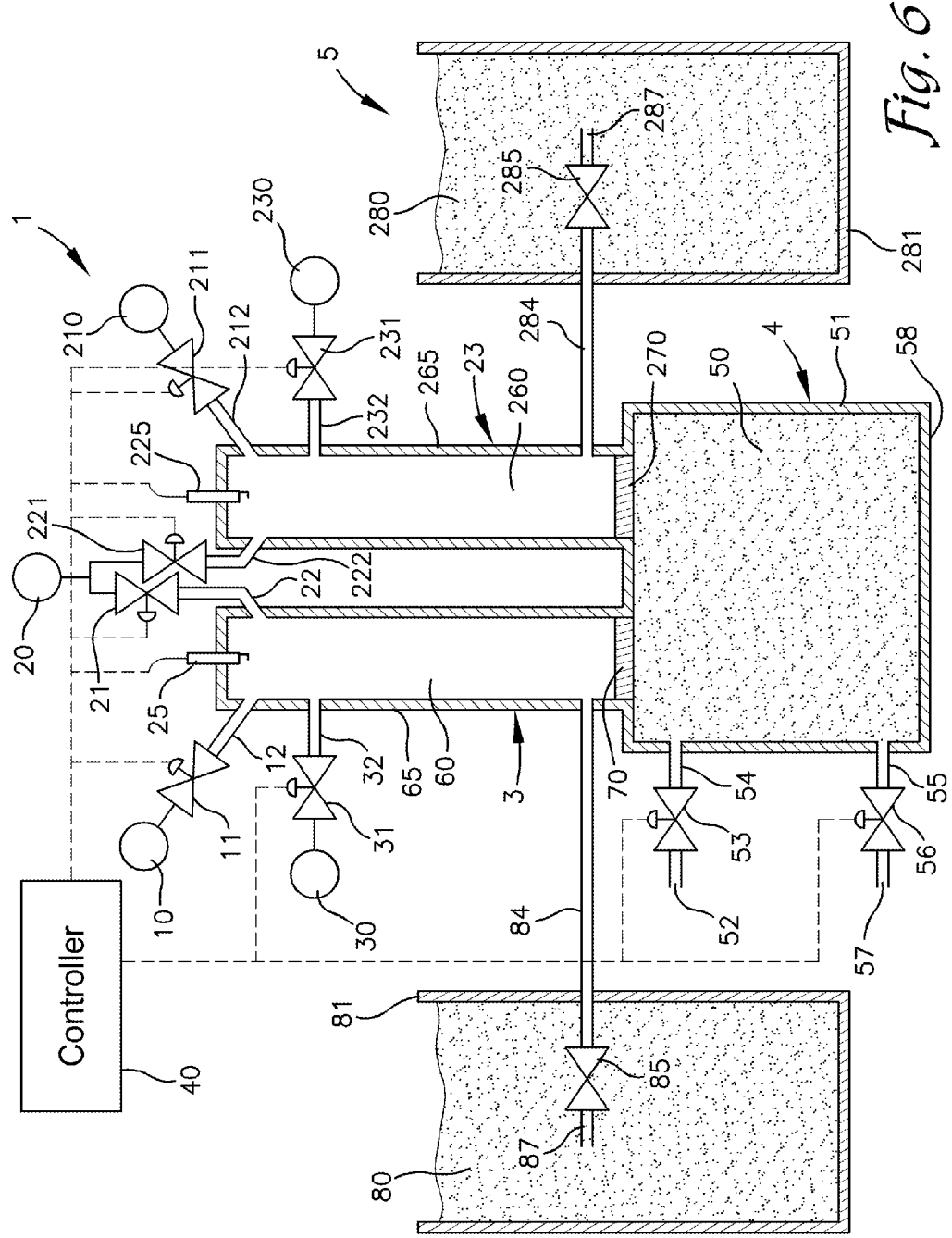
FIG. 6 is a cross-sectional schematic view of a sixth embodiment of the shockwaves processing apparatus in which multiple shockwaves generation chambers generate shockwaves in a shockwaves processing chamber and where reaction products purge lines and purge valves from each shockwaves generation chamber are immersed in separate reaction products dumping tanks.

In the embodiment shown schematically in FIG. 6, the shockwaves processing apparatus has a shockwaves generation section 3 that has two shockwaves generation chambers 60 and 260 that are similar in construction to the shockwaves generation chamber shown in FIG. 2. Reaction products from the shockwaves generation chamber 60 are 260 are purged into two separate dumping tanks. Reaction products from the chamber 60 are purged through the line 84, valve 85 and line 87 into sound and heat absorbing media filling the tank 80, where line 84, valve 85 and line 87 are fully or partially immersed in this media. Reaction products from the chamber 260 are purged through the line 284, valve 285 and line 287 into sound and heat absorbing media filling the tank 280, where line 284, valve 285 and line 287 are fully or partially immersed in this media. Thus reaction products purge section 5 for the embodiment shown in FIG. 6 has two reaction products dumping tanks 80 and 280 that can be equal or different in volume. The reaction products dumping tanks 80 and 280 can contain the same or different sound and heat absorbing media and can be ether connected through a conduit or disconnected. Alternatively, reaction products from the shockwaves generation chambers 60 and 260 can be purged in one dumping tank.

The shockwaves generation chambers 60 and 260 shown in FIG. 6 have a fuel tank 20 that is used to supply fuel that is injected into the chambers through the lines 22 and 222. The fuel injection is controlled by the valves 21 and 221 and the controller 40. The shockwaves generation chambers have also two separate igniters 25 and 225 and two oxidizer storage tanks 10 and 210. The embodiment shown in FIG. 6 has also two tanks 30 and 230 for the pressurizing gas supply. The pressurizing gas is injected into the shockwaves generation chambers trough the lines 32 and 232 and the gas injection is controlled by the valves 31 and 231. Tanks 30 and 230 can contain the same or different pressuring gases. The pressure relief valves 85 and 285 are used for purge of the pressurizing gas and the detonation products after the detonation phase of the shockwaves generation cycle. It is clear that a single gas supply tanks for each pressurizing gas and oxidizer can be used instead of two tanks as shown in FIG. 6. It is also clear that chambers 60 and 260 can use the same or different reactive mixture and same or different cycle operation parameters.

In FIG. 6 a membrane 70 is used for transmitting the shockwaves from the shockwaves generation chamber 60 into the processing chamber 50 and a membrane 270 is used for transmitting shockwaves from the shockwaves generation chamber 260 into processing the chamber 50. The elements of the shockwaves processing section 4 shown in FIG. 6 are the same as in the embodiment shown in FIG. 2. A critical advantage of the embodiment shown in FIG. 6 is that it allows using multiple shockwaves generation chambers for generation of multiple shockwaves used for processing of materials in a single processing volume. These shockwaves can be generated at the same time or at given time intervals and will create a complex pattern of shockwaves propagating through the processed media. Embodiment schematically shown in FIG. 6 may be used to generate constructive and distractive shockwave interferences which may produce large sheer forces that can induce cavitation in liquids.

As a function of detonation gas pressure containment, shockwave propagation requirements and material properties, the walls 65 and 26 thickness of the shockwaves generation chamber 60 shown in FIGS. 1 to 4 and 6 may range from 0.5 mm to 50 cm. As a function of shockwave propagation requirements, device design and material properties, the walls 51 and 58 thickness of the processing chamber 50 shown in FIGS. 1 to 4 and 6 may range from 0.5 mm to 50 cm. As a function sound and heat absorption requirements, device design and material properties the wall 81 thickness of the reaction products dumping tank 80 shown in FIGS. 1 to 6 and wall 281 thickness of tank 280 shown in FIG. 6 may range from 0.5 mm to 100 cm. The geometry of the shockwaves generation chamber 60 may be cylindrical, spherical, polyhedral, converging geometry, diverging geometry or combination of converging and diverging geometries.

As an example of one possible configuration of the shockwaves processing apparatus 1, shown schematically in FIG. 2, shockwaves generation chamber 60 and processing chamber 50 will be cylindrical and will have a 2 cm internal diameter and will be correspondingly 20 cm and 30 cm long. The walls 65 and 51 will be made of a 6 mm thick stainless steel tube. The endwalls 26 and 58 will be made from stainless steel and be 10 mm thick. The membrane 70 will be cylindrical 2 cm in diameter and 5 mm thick made from high thermal resistance silicone based composite.

The geometry of the shockwave processing chamber 50 may be cylindrical, spherical, polyhedral, converging geometry, diverging geometry or combination of converging and diverging geometries. Generally, one may use the shockwave processing chamber with a converging geometry in order to generate higher pressure shockwaves toward the distal end 58, or to compensate for the shockwave attenuation that can be especially evident in long shockwaves processing chambers. Using shockwaves processing chambers with a converging geometry where the convergence angle is designed to compensate for shockwaves attenuation in the media can allow uniform exposure of processed media to the shockwaves.

The geometry of the reaction products dumping tanks 80 and 280 may be cylindrical, spherical, polyhedral, converging geometry, diverging geometry or combination of converging and diverging geometries. The dumping tanks can be with open top allowing reaction products to vent into environment as shown in FIGS. 4, 5 and 6 or with a closed top as shown in FIGS. 1,2 and 3 venting reaction products into environment through a valve. Multiple valves or opening can be also used for venting of gases form the dumping tanks. The dumping tanks can also be constructed to have a partially open top venting reaction products into environment through an opening in the top wall, which will reduce splashing as a result of purge of a large volume of reacted gas into the media in tanks 80 and 280. The media that can be used for absorbing sound and heat produced by rapid purge of reaction products from chambers 60 and 260 is usually liquid. Also other substances can be used for sound and heat absorption such as gels, gases, multi-phase media or any combination thereof. The following are examples without limitation of sound and heat absorbing media that can be used according to various embodiments of invention: water, saline water, water with antifreeze additive, refrigerant, air, air and water and other substances allowing to partially absorb sound and heat emitted as a result of rapid purge of reacted gases form the shockwaves generation chamber Immersion of the shockwaves processing apparatus into a tank filled with liquids such as water shown in FIG. 4 present a supplementary advantage because in addition to absorbing sound and heat produces by purged reaction products, liquid in tank 80 may also absorb heat and sound emitted from other elements of the system. Full immersion will also provide additional safety for operating the system because in case of catastrophic failure of any of the system elements their fragments, which can be propelled at high velocity because of the high pressures characteristic for the system operation, can be absorbed by the liquid in the tank 80.

In FIG. 5 as a function of the detonation gas pressure containment, shockwave propagation requirements and material properties can have the walls 65, 66 and 26 thickness of the shockwaves generation section 3 range from 0.5 mm to 50 cm. As a function of shockwaves propagation requirements, device design and material properties, the walls 51 and 58 thickness of the shockwaves processing section 4 shown in FIG. 5 may range from 0.5 mm to 50 cm. As an example of one possible configuration of the shockwaves processing apparatus 1, shown schematically in FIG. 5, the shockwaves generation chamber 60 will be cylindrical and will have a 3 cm internal diameter and be 150 cm long. The walls 65 and 26 will be made of 10 mm thick tungsten carbide and wall 66 from 5 mm thick aluminum alloy. The endwall 58 will be made from stainless steel and be 10 mm thick. The shockwaves processing section 4 will have a cylindrical processing chamber 50 with 6 cm internal diameter and will be 150 cm long. The wall 51 will be made from 4 mm thick stainless steel, consequently the distance between the external surface of the wall 66 and the internal surface of the wall 51 will be 10 mm and the volume of the processing section in this embodiment will be approximately 2.3 liters.

The various embodiments of the shockwaves processing apparatus, produce high intensity shockwaves in the shockwaves generation chamber 60 that may transmit into liquid or suspension in the processing chamber 50 through an interface, a membrane or directly. The operational parameters such as initial pressure, reactive mixture composition, ignition discharge energy, initial temperature of the reactive mixture, injection and ignition timing are selected so to create the required processing effect. The shockwaves processing apparatus as disclosed herein provide scalable, safe, and cost effective apparatus and methodology that allows using a detonable or other reactive mixture that can be repeatedly injected into a shockwaves generation chamber 60 that is designed to contain detonation products and transmit shockwaves into media located in a processing chamber 50. According to various embodiments of invention shockwaves generation processes will have small acoustic signature and will be protected from over-heating because of immersion of its system element into sound and heat absorbing media that is filling reaction products dumping tank 80. The shockwaves generation chamber 60 of the shockwaves processing apparatus 1 can be pressurized with a compressed air at 1 MPa pressure and then filled with a stoichiometric mixture of oxygen and natural gas at 2 MPa initial pressure and approximately 0.03 g/cc initial density. This mixture is detonable thus initiation with the spark plug 25 will cause detonation. The resulting detonation wave will create a shockwave in the shockwaves generation section 3. A detonation wave propagating through a 2 MPa detonable mixture of oxygen and natural gas will have approximately 70 MPa peak pressure, approximately 2 km/sec shockwave velocity, and approximately 0.2 g/cc peak density. After shockwaves generation chamber 60 will be filled with mostly gaseous reaction products at approximately 24 MPa and 4000° K. These reaction products may be purged into reaction products dumping tank filled with water leading to absorption of sound and heat produced by the discharge of these gases. Due to use of pressurizing gas and reaction products dumping tank the shockwaves generation cycle may be repeated at 0.001 Hz to 1000 Hz wave generation frequencies.

The amount of shockwave energy transmitted to the media located in the shockwaves processing section 4 is a function of the media impedance. Using shown in FIG. 4 converging nozzle 100 may allow multi fold amplification of the shockwave pressure thus enhancing its processing effect in the processing chamber 50. This shockwave may propagate through water in the chamber 50 and may result in killing of most microorganisms such as gram positive and gram negative bacteria, disrupting various types of algae and producing other mechanical, chemical and biological effects that are known to be caused by shockwaves. High pressure may be also generated by increasing the initial pressure in chamber 60 and selecting reactive mixture that produce detonations with higher pressure. Appropriate selection or reactive mixture, initial pressure and shockwaves generation chamber/nozzle design may allow generation of hydrodynamic shockwaves in the processing chamber 50 shown in FIGS. 1 to 4 for example with pick pressure over 900 MPa which may be most efficient for the shockwaves processing of liquids, suspensions, pastes pasteurization and sterilization. Various embodiments of our invention may allow generating these high peak pressure shockwaves safely with effective suppression of sound and absorption of heat produced during the processes which in turn can enable industrial implementation of this technology.

The physical, biological and chemical effects produced by the shockwaves are function of peak pressure and shockwave impulse. The peak pressure of the shockwaves propagating in the shockwaves generation chamber 60 are mostly controlled by the initial density, pressure, energy density of the reactive mixture, mixture reaction rate, the chamber geometry and other parameters. The shockwave impulse is a function of the parameters of the detonable mixture as well as design and size of the shockwaves generation chamber 60. Various embodiments of the shockwaves processing apparatus illustrated in FIGS. 1 to 6 allow design of the shockwaves generation section 3 where standard methods can be suitably selected by persons skilled in the art with the aid of no more than routine experimentation to produce impulse and shockwave structure in term of pressure time history that is most appropriate for the processing needs.

Examples of use of various embodiments of the processing apparatus disclosed herein include:
- Food pasteurization and sterilization
- Nucleation of polymers
- Cell lysis
- Inactivation of pathogens used for vaccine preparation
- Inactivation of cancer cell for immunotherapy
- Genetic transfection
- Genetic transformation
- Processing that increase cells permeably
- Processing of seeds in water or other solutions to increase germination
- Processing of waste suspension to increase methane production
- Milling
- Homogenization
- Processing to control fermentation
- Processing for scientific experimentation There are critical advantages in the use of shockwaves processing apparatus according to various and alternative embodiments of present invention.

One of the critical advantages of described here shockwaves processing apparatus is to allow processing large volumes of liquid or liquid suspension media at approximately uniform processing conditions which is very important for a number of applications such as material processing, pasteurization, cell lysis and fermentation control. Another advantage that processing may be performed without a significant temperature increase during apparatus operation and may be used for non-thermal pasteurization.

Another critical advantage of various alternative embodiments of described here shockwaves processing apparatus is its scalability to a wide range of sizes based on processing needs. The sizes of the shockwaves generation section 3, the shockwaves processing section 4 and the reaction products purge section 5 in the embodiments shown schematically in FIGS. 1 through 6 can be selected to accommodate processing needs in terms of shockwaves amplitude and duration designed to produce designed processing effect. For example, and without limitation, the shockwaves generation chamber 60 and the processing chamber 50 each can have volumes of 1 $cm^3$ to 1000 $cm^3$ for generation of shockwaves and processing liquids in a small scale shockwave processing apparatus that is used for scientific or industrial tests or 1 liter to 10000 liters for a shockwaves processing apparatus used for industrial pasteurization of milk or juice. The dumping tank 80 can have volume of 1 liter to 10000 liters. Also natural or artificial fresh or saltwater reservoir or source can be used as a dumping tank. Without limitation, the length of the shockwaves generation chamber 60 and wall 65 can be 1 cm to 10 m long and 1 mm to 5 m diameter, where the length of the processing chamber 50 and wall 51 can also be 1 cm to 10 m long and 1 mm to 5 m diameters and dumping tank wall 81 shown in FIG. 3 10 cm to 10 m long and 5 cm to 50 m diameter. Based on processing needs, the shockwaves generation chamber 60 and the processing chamber 50 may have one of the following: equal volumes; the shockwaves generation chamber may have a volume that is larger than the processing chamber; or the shockwaves generation chamber may have a volume that is smaller than that of the processing chamber. Dumping tank may be made at various sizes.

Another critical advantage of various alternative embodiments of described here shockwaves processing apparatus is its ability to generate shockwaves and acoustic waves with a wide range of parameters emitting very low noise into environment.

The shockwaves generation chamber 60 can be filled with detonable reactants to provide a detonable mixture with an initial density that may range from 0.1 to 1800 kg/m3. Reaction of these mixtures in a detonative process or other rapid reaction process in the shockwaves generation chamber can generate shockwaves and/or acoustic waves in the processing chamber 50 with peak pressure in the range of 1 to 5000 mega pascals (MPa) and, preferably, between 10 and 2000 MPa. Using standard methods these shockwaves can be designed to have positive phase duration of 10 nanoseconds to 1 millisecond.

The design of the shockwaves generation chamber 60 can be implemented in various geometries that allow shockwave reflections and focusing or transmitting with different shockwave or acoustic wave profiles of pressure as a function of time. The design of the processing chamber 50 can be implemented to allow focusing and multiple reflections of the transmitted shockwaves that can enhance the efficiency of the shockwaves processing.

To facilitate pressure containment and reflections of the shockwaves the shockwaves generation chamber can be made for example from materials with high strength and high impedance, such as metals, cermets, ceramics, polymers, fiber based composites, and combination thereof.

To facilitate transmission of the shockwaves from the shockwaves generation chamber to the processing chamber the membrane or other material that serves as an interface between the reaction products of the shockwaves generation chamber and the liquid of the processing chamber can be made for example from materials with high strength and low impedance, such as polymers, suitable fiber-based composites, and thin high-strength materials such as steel and combinations thereof allowing wave transmission from the shockwaves generation chamber to the processing chamber.

To facilitate multiple reflections of transmitted into liquid shockwaves and acoustic waves that will reduce shockwave energy losses, the walls of the components of the processing chamber can be made for example from materials with high impedance such as tungsten, tungsten carbide, steel, cermets, ceramics, and combinations thereof. To increase wave reflection effectiveness, the wall thickness of the shockwaves generation and processing chambers can be suitably selected by persons skilled in the art.

To facilitate heat and sound absorption dumping tank 80 can be made from, plastic, concrete, composite, metal, cermets or other materials that are used for construction of pools, water reservoirs. Also natural or artificial water reservoir can be used as reaction products dumping tank.

To enhance the killing of microorganisms and/or to take advantage of increased cell walls permeability, prior or during treatment with the shockwaves processing apparatus, the liquid or liquid suspension to be treated may be injected with small gas bubbles, drugs, viruses, genome segments, chemicals, nanoparticles and other reagents. The gas bubbles may reduce effective impedance of the processed media and produce additional sheer force on bacteria during and after shockwave propagation, and can produce additional shockwaves due to bubble collapse. These effects may lead to enhanced killing of cells or microorganisms. It is understood that air or other gases can be used for generating gas bubbles in processed media. Also changing temperature of the liquid in chamber 50 prior to shockwaves processing can increase shockwaves processing effect. For example, cooling juice to near 0° C. may allow more effective pasteurization using shockwaves. The same effect can be achieved by heating juice in processing chamber 50 to 60° C. before exposure to shockwaves.

It is also understood that the shockwaves processing apparatus design without limitation can include multiple shockwaves generation chambers operating simultaneously or with a pre-determined time delay that are used for processing materials in a single processing chamber as shown in FIG. 6. These multiple shockwaves generation chamber can have a single or multiple ignition sources, use single or multiple fuel, oxidizer, and pressurizing gas sources. Use of multiple shockwaves generation chamber can be used to create a spectrum of shockwaves in the processing chamber with deferent parameters, to increase intensity of processing by the interacting shockwaves and high amplitude acoustic waves, to increase shockwaves generation frequency and thus processing capacity of the shockwaves processing system. A person skilled in the art can also design a shockwaves processing apparatus with multiple shockwaves generation chambers that generate shockwaves in the processing chamber that can propagate in normal direction to each other or at some predetermined angle allowing generation of the high intensity shockwaves and acoustic waves as a result of constructive and destructive interference between the waves that are emitted into a processing chamber. The interfering waves can be also beneficial for producing sheer force that will be effective for milling, cell lysis and killing microorganisms.

It is also understood that the shockwaves processing apparatus can be implemented in cylindrical, conical, semi-spherical forms or in form of a prism.

It is also understood that for specific processing need multiple shockwaves processing devices can operate simultaneously, with or without synchronized time delay.

It is also understood that for controlling gas, liquid and liquid suspension injection and gas relief processes persons skilled in the art may select valves of different construction such as solenoid valves, rotary valves, piezoelectric valves, hydraulic valves, mechanical and others. These valve may be controlled through signals delivered to the valves by wires, wirelessly, mechanically or other methods. A person skilled in the art can also design operation of the shockwaves processing apparatus where some or all valves will be replaced by properly designed openings in the walls of the chambers that will control for example pressure relief of the exhaust gas. The detonation ignition process can be facilitated by various ignition methods such as a spark plug, laser, glow plug and plasma jet ignition. Where laser ignition can be used for ignition of reactive mixtures with high initial pressure at the conditions that are difficult to ignite with spark plugs.

It is also understood that multiple valves can be used, instead of single valves for a particular processing function shown in FIGS. 1 to 6. For example, multiple purge valves attached to multiple openings can be used to assure rapid purge of gas from the shockwaves generation chamber 60. Multiple valves operating simultaneously or with a designed time sequence can be used for the pressurizing gas, oxygen and fuel injection to increase injection flow rate, reduce thermal load and increase process reliability.

It is also understood that it is possible to implement pressurization phase of the shockwave generation cycle by injection of ether oxidizer or fuel trough oxidizer or fuel feed lines thus avoiding a separate injection of the pressurizing gas. This form of implementation may use more expensive gases and may be less efficient in purging of the detonable products and in avoiding self-ignition.

While various embodiments of the present invention have been disclosed, it will be apparent to those of ordinary skill in the art that many more embodiments and implementations are possible within the scope of the invention. For example, the present invention as described herein includes several aspects and embodiments that include particular features. Although these features may be described individually, it is within the scope of the present invention that some or all of these features may be combined with any one of the aspects and remains within the scope of the invention. Accordingly, the present invention is not to be restricted except in light of the attached claims and their equivalents.

What is claimed is:

1. A method for processing liquids, liquid suspension, colloids, gels, pastes comprising the steps of:
    providing a shockwaves processing apparatus comprised of a shockwaves generation section with a shockwaves generation chamber; a shockwaves processing section, connected to said shockwaves generation section, with a shockwaves processing chamber; a reaction products dumping tank or reservoir, connected to said shockwaves generation section via a conduit or conduits, at least partially filled with sound and heat absorbing media;
    placing media to be processed into the shockwaves processing section through continuous or intermittent injection;
    introducing a pressurizing gas into the shockwaves generation section through continuous or intermittent injection;
    introducing a mixture comprised of a detonable mixture or a reactive mixture into the shockwaves generation section;
    causing formation of at least one of a shockwave within the shockwaves generation section by igniting the detonable mixture or causing a reaction of the reactive mixture so that at least one of a shockwave or an acoustic wave propagates from the shockwaves generation section into the shockwaves processing section;
    utilizing physical, chemical, biological or mechanical effects of the shockwave, shockwaves or acoustic waves propagating in the shockwaves processing section to alter physical, chemical, biological or mechanical properties of the media located in the processing section;

purging reaction products and pressurizing gas from the shockwaves generation section into the reaction products dumping tank or reservoir; and repeating introducing the pressurizing gas followed by the detonable mixture and causing formation of at least one shockwave as many times as needed for achieving a pre-determined degree of processing liquids, liquid suspensions, colloids, gels, or pastes located in the shockwaves processing section.

2. The method of claim 1, wherein the pressurizing gas is air, nitrogen, oxygen or any other gas or mixture of gases that prevent self-ignition of detonable or reactive mixture injected into the shockwaves generation section.

3. The method of claim 1, wherein the pressurizing gas is heated or cooled before injection into the shockwaves generation chamber.

4. The method of claim 1, wherein the pressurizing gas is formed by injection of a liquid into the shockwaves generation section.

5. The method of claim 1, wherein the reaction products and the pressurizing gas are exhausted into the reaction products dumping tank or reservoir through a single or multiple solenoid valves, piezoelectric valves, mechanical valves or orifices.

6. A method for processing liquids, liquid suspension, colloids, gels, pastes comprising the steps of:
providing a shockwaves processing apparatus comprised of a shockwaves generation section with a shockwaves generation chamber; a shockwaves processing section, connected to said shockwaves generation section, with a shockwaves processing chamber; a reaction products dumping tank or reservoir, connected to said shockwaves generation section via a conduit or conduits, at least partially filled with sound and heat absorbing media;
placing media to be processed into the shockwaves processing section through continuous or intermittent injection;
introducing a mixture comprised of a detonable mixture or a reactive mixture into the shockwaves generation section;
causing formation of at least one of a shockwave within the shockwaves generation section by igniting the detonable mixture or causing a reaction of the reactive mixture so that at least one of a shockwave or an acoustic wave propagates from the shockwaves generation section into the shockwaves processing section;
utilizing physical, chemical, biological or mechanical effects of the shockwave, shockwaves or acoustic waves propagating in the shockwaves processing section to alter physical, chemical, biological or mechanical properties of the media located in the processing section;
purging reaction products from the shockwaves generation section into the reaction products dumping tank or reservoir; and
repeating introducing the detonable mixture and causing formation of at least one shockwave as many times as needed for achieving a pre-determined degree of processing liquids, liquid suspension, colloids, gels, or pastes located in the shockwaves processing section.

7. The method of claim 1 or 6, wherein the reactive mixture introduced into the shockwaves generation section undergoes at least one process selected from the group consisting of detonation, deflagration, transition from deflagration to detonation, rapid decomposition, and combinations thereof that result in formation of at least one shockwave in the shockwaves generation section.

8. The method of claim 1 or 6, wherein the sound and heat absorbing media used in the reaction products dumping tank or reservoir is water, saline water, antifreeze, water and antifreeze mixture, refrigeration cooling agent, or any other liquid or mixture of gases and liquid suspension that absorbs sound and heat.

9. The method of claim 1 or 6, wherein the shockwaves processing apparatus is fully or partially immersed into the media in the reaction products dumping tank or reservoir.

10. The method of claim 1 or 6, wherein one or a number of reactants of the detonable mixture are heated or cooled before injection into the shockwaves generation chamber.

11. The method of claim 1 or 6, wherein the media to be processed is cooled or heated prior to introduction into the processing chamber or when located in the processing chamber.

12. The method of claim 6, wherein the reaction products are exhausted into the reaction products dumping tank or reservoir through a single or multiple solenoid valves, piezoelectric valves, mechanical valves or orifices.

13. The method of claim 1 or 6, wherein the shockwaves processing section has a geometry selected from the group consisting of a converging geometry, a diverging geometry, a variable cross section geometry, a constant cross section geometry and any combination of converging, diverging, constant and variable cross section geometries.

14. The method of claim 1 or 6, wherein the shockwaves generation section has a geometry selected from the group consisting of a converging geometry, a diverging geometry, a variable cross section geometry, a constant cross section geometry and any combination of converging, diverging, constant and variable cross section geometries.

15. The method of claim 1 or 6, wherein the shockwaves generation section is separated from the shockwaves processing section by a movable interface that separate media in the shockwaves generation chamber and the shockwaves processing chamber.

16. The method of claim 1 or 6, wherein the shockwaves generation section is separated from the shockwaves processing section by a membrane made of materials that facilitate containment of pressure and at least partially transmit one of the shockwaves or acoustic waves.

17. The method of claim 1 or 6, wherein the shockwaves generation section is separated from the shockwaves processing section by a membrane made of materials that facilitate containment of pressure with at least one membrane surface facing the shockwave generation chamber and at least partially transmit at least one of the shockwaves or acoustic waves, and wherein the membrane surface facing the shockwaves generation chamber is fully or partially covered with liquid.

18. The method of claim 1 or 6, wherein the shockwaves generation section is made of multiple shockwaves generation chambers used to generate shockwaves and the shockwaves processing section is made of a single processing chamber, wherein igniting the detonable mixture or causing a reaction of the reactive mixture within the shockwaves generation chambers is performed simultaneously or sequentially in a timed manner.

19. A method for processing liquids, liquid suspension, colloids, gels, pastes comprising the steps of:
providing a shockwaves processing apparatus comprised of a shockwaves generation section with walls having external and internal surfaces; a shockwaves processing section, connected to said shockwaves generation section, at least partially filled with media to be processed; a reaction products dumping tank or reservoir, connected to said shockwaves generation section via a conduit or conduits, wherein the external surface of the wall of the shockwaves generation section is at least partially immersed in the media to be processed;

introducing a pressurizing gas into the shockwaves generation section through continuous or intermittent injection;

introducing a mixture comprised of a detonable mixture or a reactive mixture into the shockwaves generation section;

causing formation of at least one of a shockwave within the shockwaves generation section by igniting the detonable mixture or causing a reaction in the reactive mixture so that at least one of shockwave or acoustic wave propagates from the shockwaves generation section into the shockwaves processing section;

utilizing physical, chemical, biological or mechanical effects of the shockwave, shockwaves or acoustic waves propagating in the shockwaves processing section to alter physical, chemical, biological or mechanical properties of the media located in the processing section;

purging reaction products and pressurizing gas from the shockwaves generation section into the reaction products dumping tank or reservoir; and repeating introducing the pressurizing gas followed by the detonable mixture and causing formation of at least one shockwave as many times as needed for achieving a pre-determined degree of processing liquids, liquid suspension, colloids, gels, or pastes located in the shockwaves processing section.

20. The method of claim 19, wherein at least one wall of the shockwaves generation section is made of materials that facilitate containment of pressure and at least partially transmit at least one shockwave and acoustic wave, and wherein the external surface of the wall of the shockwaves generation section is at least partially immersed within the media contained in the shockwaves processing section.

21. The method of claim 19, wherein the shockwaves generation section is made of multiple shockwaves generation chambers wherein the external surfaces of the walls of said chambers are at least partially immersed within the media contained within the shockwaves processing section, wherein the walls of the multiple shockwaves generation chambers are made of materials that facilitate containment of pressure and partially transmit at least one shockwave and acoustic wave, and wherein igniting the detonable mixture or causing a reaction in the reactive mixture within the shockwaves generation chambers is performed simultaneously or sequentially in a timed manner.

* * * * *